(12) United States Patent
Deshlahra et al.

(10) Patent No.: US 12,202,795 B2
(45) Date of Patent: Jan. 21, 2025

(54) GAS-PHASE HOMOGENEOUS OXIDATIVE DEHYDROGENATION AND COUPLING OF ORGANIC MOLECULES

(71) Applicant: Trustees of Tufts College, Medford, MA (US)

(72) Inventors: Prashant Deshlahra, Somerville, MA (US); Leelavathi Annamalai, Newark, DE (US)

(73) Assignee: Trustees of Tufts College, Medford, MA (US)

( * ) Notice: Subject to any disclaimer, the term of this patent is extended or adjusted under 35 U.S.C. 154(b) by 887 days.

(21) Appl. No.: 17/287,758

(22) PCT Filed: Nov. 1, 2019

(86) PCT No.: PCT/US2019/059332
§ 371 (c)(1),
(2) Date: Apr. 22, 2021

(87) PCT Pub. No.: WO2020/092871
PCT Pub. Date: May 7, 2020

(65) Prior Publication Data
US 2021/0395171 A1    Dec. 23, 2021

Related U.S. Application Data

(60) Provisional application No. 62/754,112, filed on Nov. 1, 2018.

(51) Int. Cl.
*C07C 5/48* (2006.01)
*B01J 21/08* (2006.01)
(Continued)

(52) U.S. Cl.
CPC ............. *C07C 5/48* (2013.01); *B01J 21/08* (2013.01); *B01J 23/22* (2013.01); *C07D 301/08* (2013.01);
(Continued)

(58) Field of Classification Search
CPC .. B01J 21/08; B01J 21/16; B01J 23/22; C07C 29/50; C07C 5/48; C07D 301/08; C07D 303/04
See application file for complete search history.

(56) References Cited

U.S. PATENT DOCUMENTS 5,877,330 A * 3/1999 Kishimoto .............. C07C 45/36
549/240
10,669,218 B2 * 6/2020 Mamedov ................ B01J 23/10
(Continued)

FOREIGN PATENT DOCUMENTS

WO    WO-2015/084576 A2    6/2015
WO    WO-2018/148145 A1    8/2018
(Continued)

OTHER PUBLICATIONS

Burch et al. "Role of Chlorine in Improving Selectivity in the Oxidative Coupling of Methane to Ethylene." Applied Catalysis, 46 (1989) 69-87. (Year: 1989).*

(Continued)

*Primary Examiner* — Sharon Pregler
(74) *Attorney, Agent, or Firm* — Foley Hoag LLP; Dana M. Gordon; David S. Surry

(57) ABSTRACT

Disclosed are gas-phase ODH and OCP processes for converting alkanes (e.g., $C_2H_6$ and $C_3H_8$) to alkenes (e.g., $C_2H_4$ and $C_3H_6$) or oxygenates (e.g., methanol, ethanol, isopropanol, or propylene oxide) or converting alkenes (e.g., ethylene and propene) and oxygenates (e.g., methanol, ethanol, isopropanol or propylene oxide) to longer carbon-chain (Continued)

alkenes or longer carbon-chain alkanes with or without solid catalysts.

25 Claims, 26 Drawing Sheets

(51) Int. Cl.
    *B01J 23/22* (2006.01)
    *C07D 301/08* (2006.01)
(52) U.S. Cl.
    CPC ...... *C07C 2521/08* (2013.01); *C07C 2523/22* (2013.01)

(56) References Cited

U.S. PATENT DOCUMENTS

2013/0137914 A1   5/2013   Struelens et al.
2018/0290950 A1  10/2018  Hermans et al.
2018/0297914 A1* 10/2018  Aljundi ............... B01J 37/0009

FOREIGN PATENT DOCUMENTS

WO   WO-2020/092871 A2   5/2020
WO   WO-2020/092871 A3   7/2020

OTHER PUBLICATIONS

Journal article (Year: 1989).*
Grant et al., "Selective oxidative dehydrogenation of propane to propene using boron nitride catalysts," Science, 354(6319):1570-1573 (2016).
International Search Report and Written Opinion for International Application No. PCT/US2019/059332 dated Jan. 17, 2020.
Otsuka et al., "Peroxide anions as possible active species in oxidative coupling of methane," Chemistry Letters, 16(1):77-80 (1987).

* cited by examiner

Fig. 1A
Fig. 1B
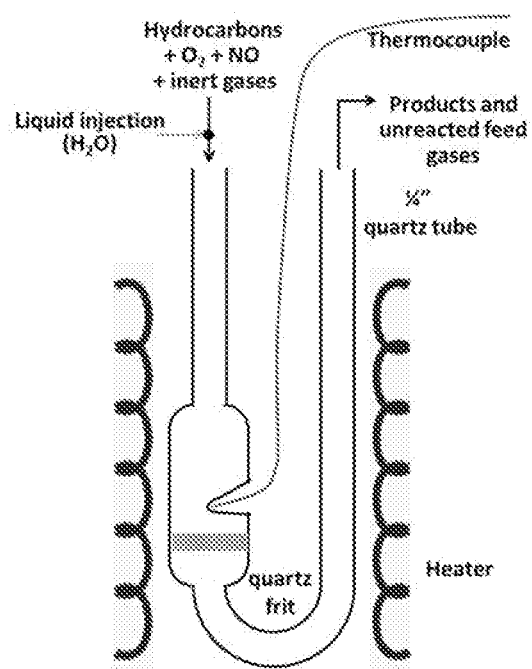
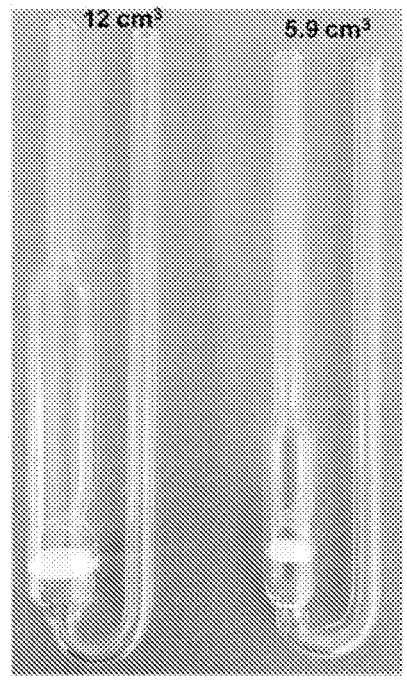

Fig. 6A
Fig. 6B
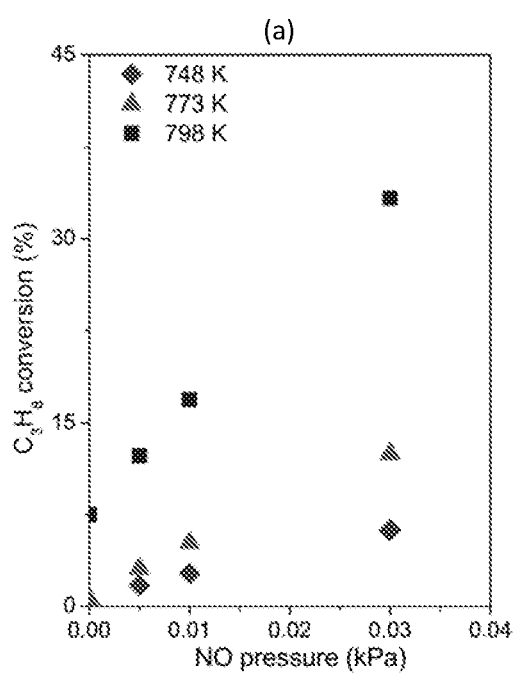
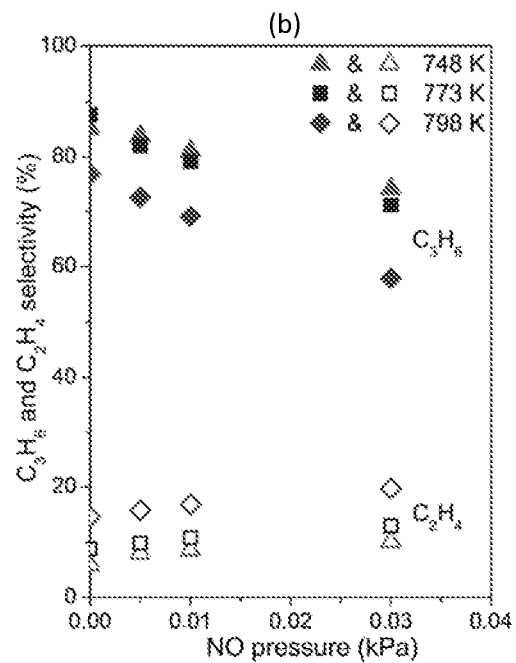

Fig. 9A
Fig. 9B
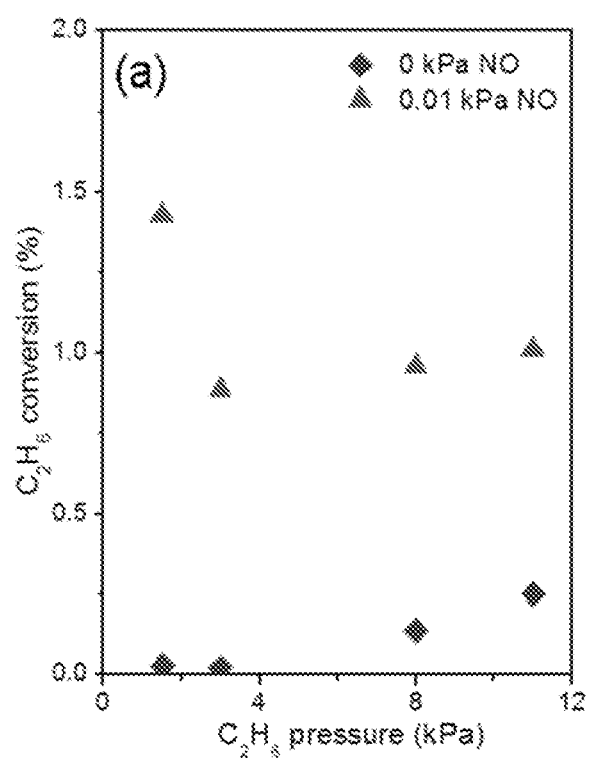
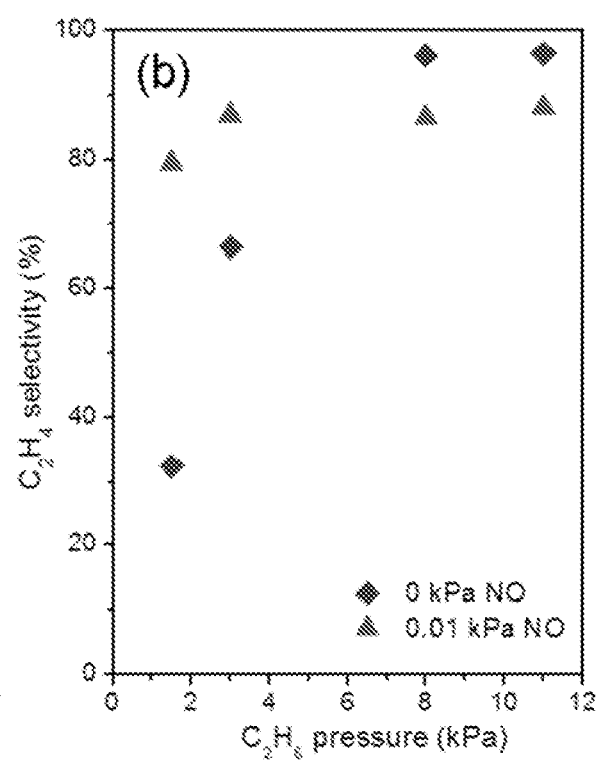

Fig. 10A
Fig. 10B
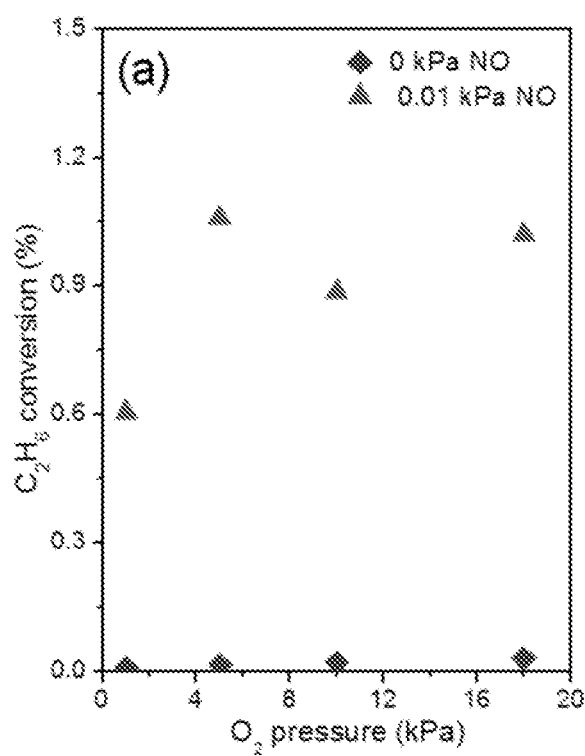
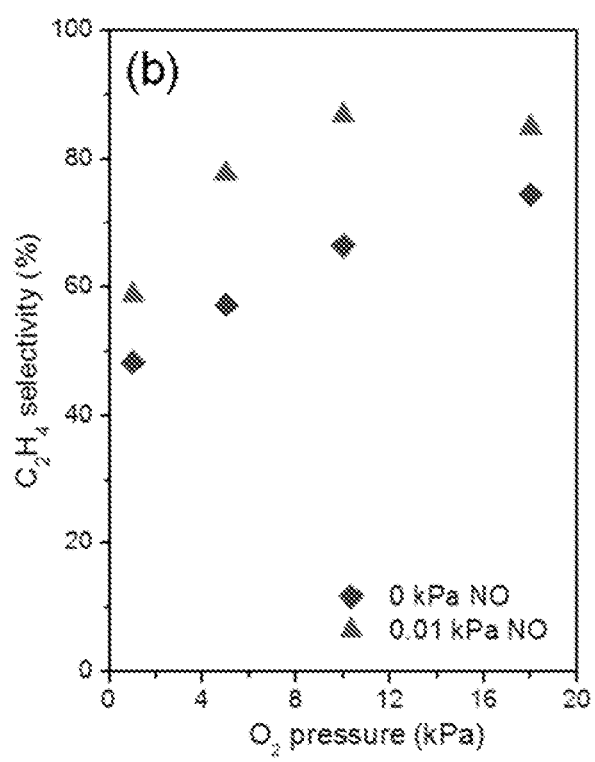

Fig. 11A
Fig. 11B
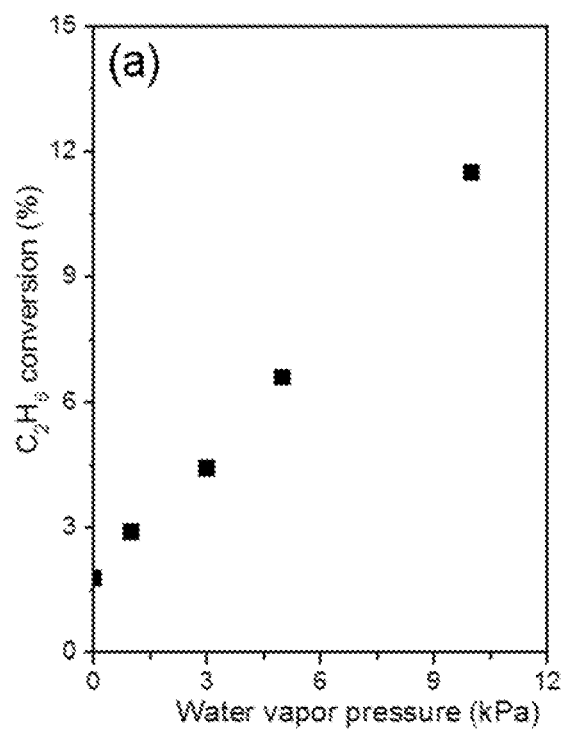
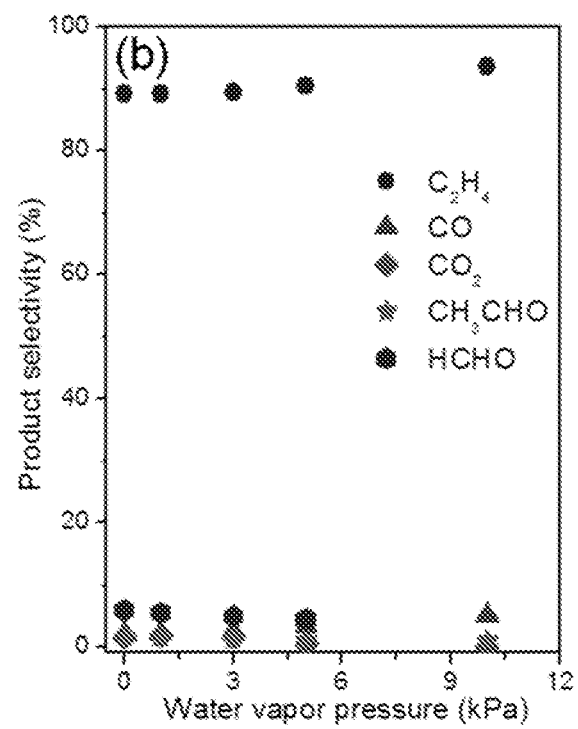

Fig. 17A
Fig. 17B
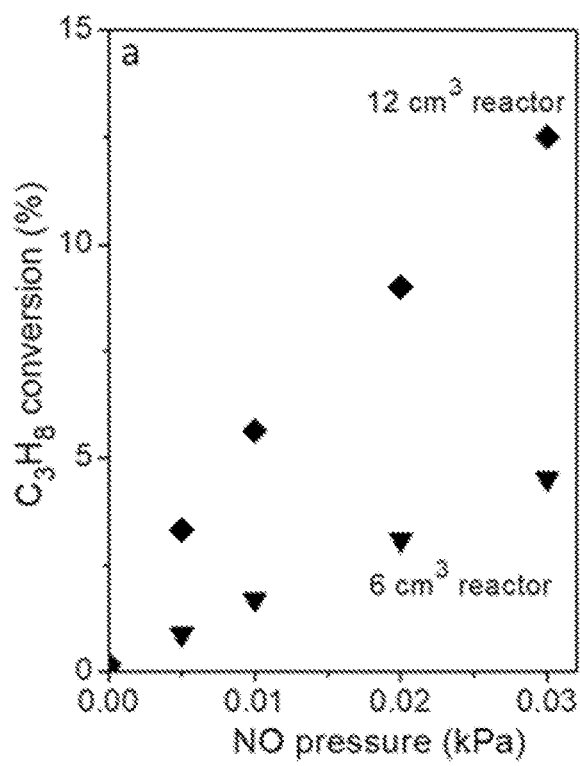
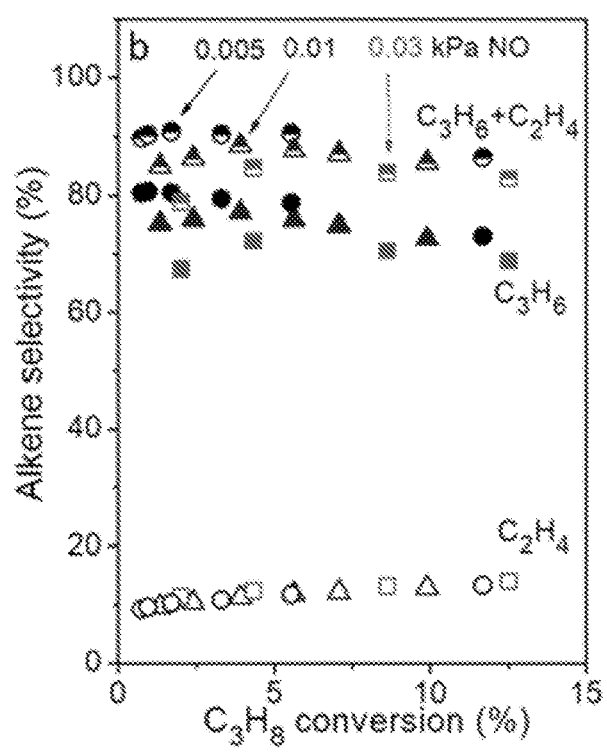

Fig. 20A
Fig. 20B
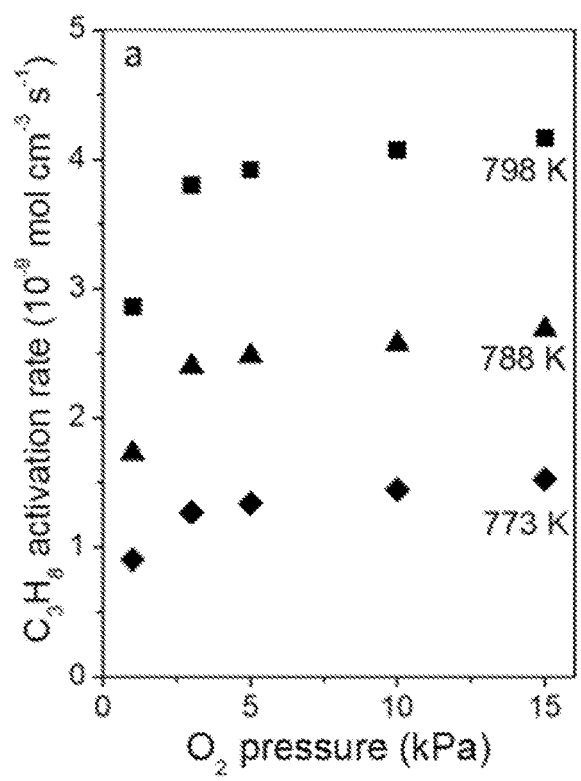
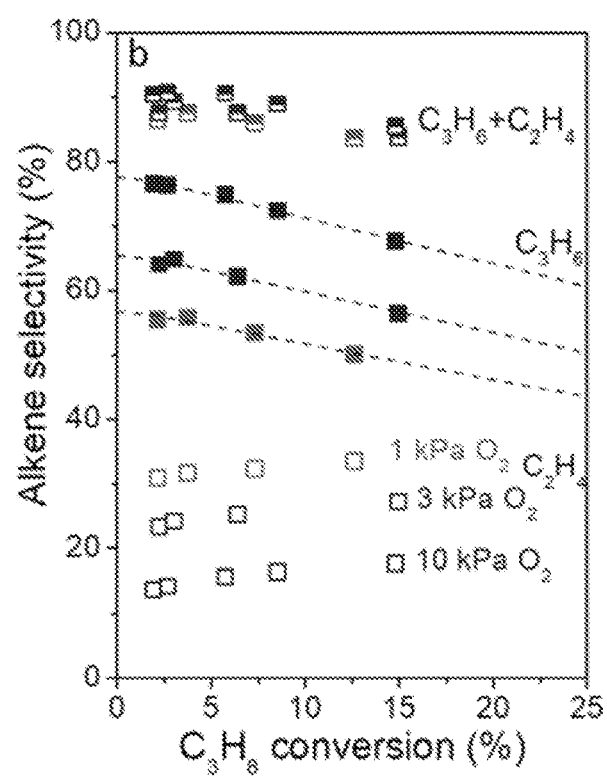

Fig. 21A
Fig. 21B
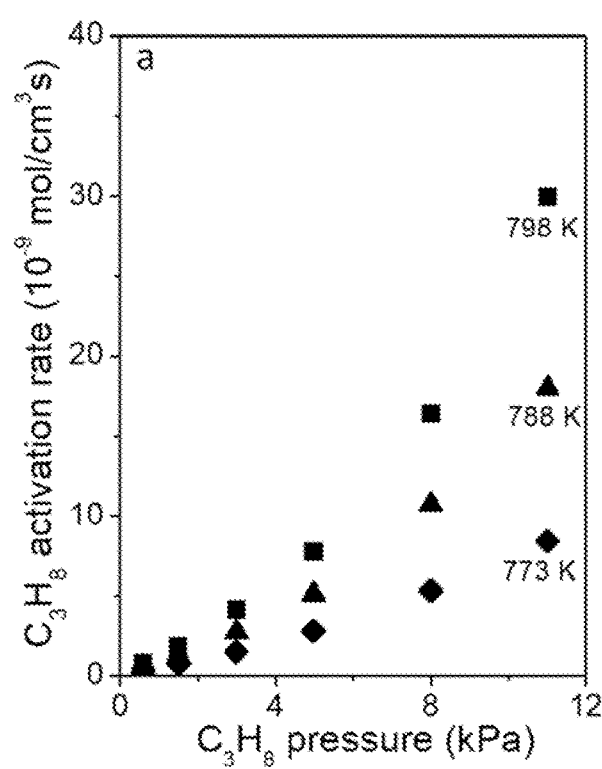
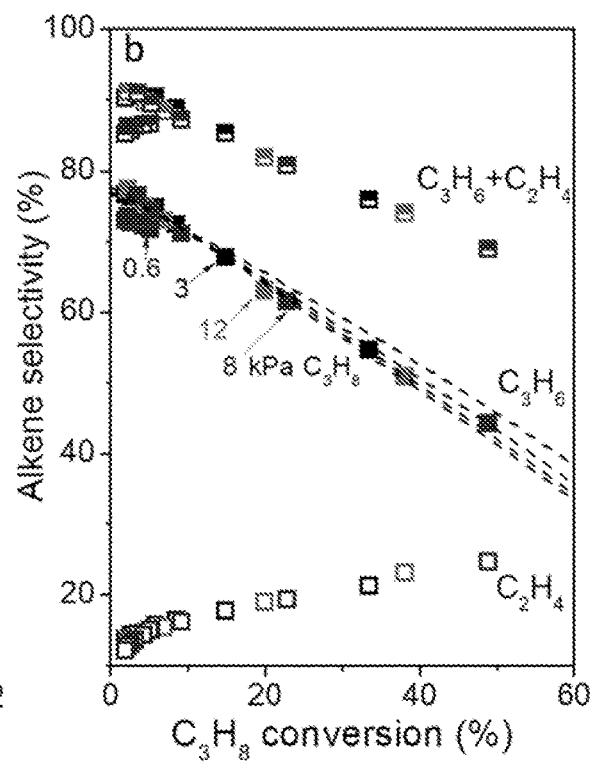

Fig. 24A
Fig. 24B
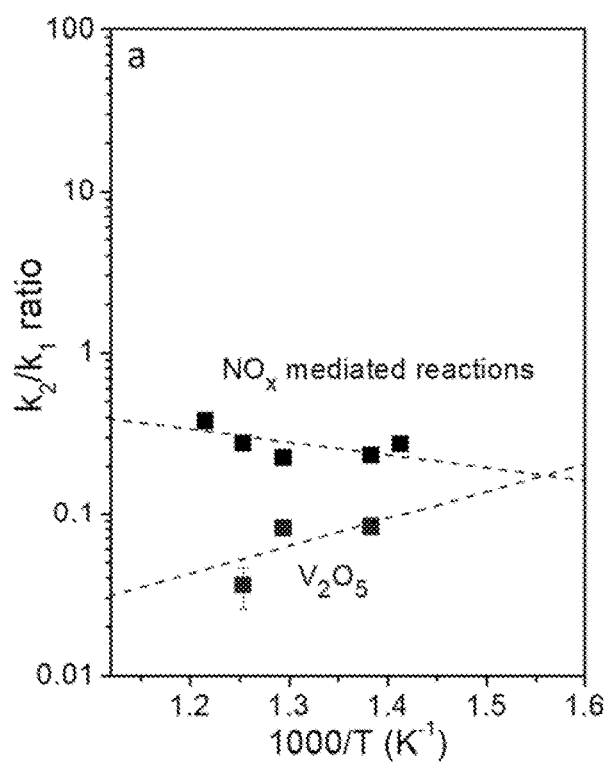
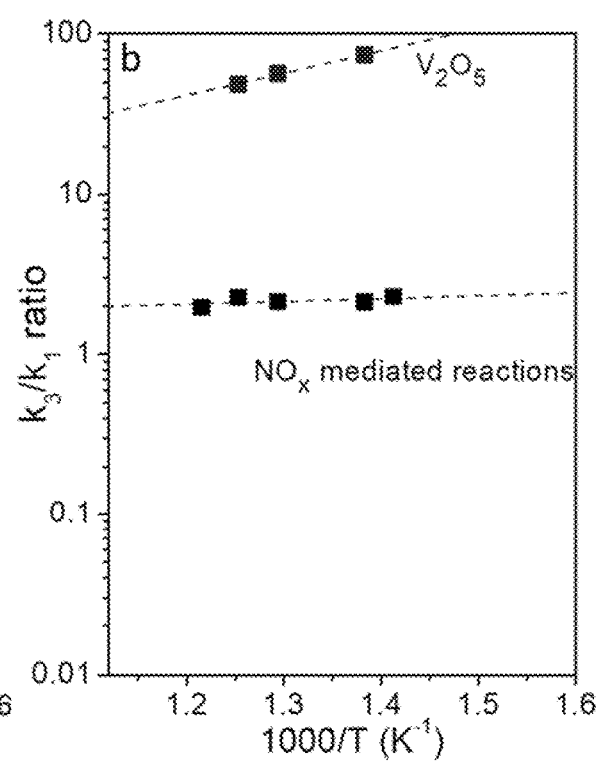

GAS-PHASE HOMOGENEOUS OXIDATIVE DEHYDROGENATION AND COUPLING OF ORGANIC MOLECULES

RELATED APPLICATIONS

This application is the National Stage of International Patent Application No. PCT/US2019/059332, filed Nov. 1, 2019; which claims the benefit of priority to U.S. Provisional Application No. 62/754,112, filed Nov. 1, 2018.

GOVERNMENT SUPPORT

This invention was made with government support under grant 1803798 awarded by the National Science Foundation. The government has certain rights in the invention.

BACKGROUND

Light alkenes, such as ethylene, propylene, butylene, and isobutylene, are important commodity chemicals used for preparing polymers (e.g., polyethylene and polypropylene), oxygenates (e.g., acrylic acid, aldehyde, and glycol), and important chemical intermediates (e.g., ethyl benzene, acetonitrile, and acrylonitrile).

Conventionally, light alkenes are prepared by steam cracking or fluid catalytic cracking of naphtha, light diesel, and other oil byproducts. Yet, these cracking processes are energy intensive due to their endothermic nature.

Typical catalytic oxidative dehydrogenation (ODH) reactions have potential as moderate-temperature energy-efficient processes for alkene production due to their exothermic nature. The major limitation of such processes is low selectivity for alkene products. Also, highly reactive and selective solid catalysts for ODH are often complex mixed oxides containing molybdenum and vanadium. The complexity of catalysts and associated costs make commercialization of these ODH processes difficult.

Modified ODH processes have been developed to improve selectivity. These processes, allowing alkane-oxygen reactions with high selectivity for alkene products, occur via the generation of gas-phase radicals, e.g., ·OH, which are strong abstractors of H atoms in alkane. Conventional generation of H-abstracting gaseous radicals occurs at very low rates or concentrations in homogeneous alkane-oxygen mixtures. It requires very high temperature (e.g., 1073 K) and solid materials to promote radical generation.

There remains a need for improved ODH processes that are more efficient and lower in operating temperature and in cost.

SUMMARY

Improved gas-phase ODH and oxidative coupling (OCP) processes for preparing alkenes are disclosed herein.

The ODH process, which incorporates an exothermic homogeneous gas-phase ODH reaction with or without a solid catalyst, has the advantages of moderate reaction temperatures, high selectivity, high yield, and little or no carbon-deposition. Turning to the OCP process, it incorporates an exothermic gas-phase oxidative coupling of a less valuable alkene and oxygenate to make a more valuable alkene with more carbon atoms per molecule than the feed alkene.

One aspect of the present invention relates to a homogeneous gas-phase ODH process for converting an alkane to an alkene or an oxygenate. Another aspect relates to a homogeneous gas-phase OCP process for converting an alkene and an oxygenate to a longer carbon-chain alkene or a longer carbon-chain alkane. A further aspect of the invention relates to a gas-phase OCP process for converting a first hydrocarbon feedstock, comprising a lower alkane or a lower alkene and an oxygenate, to a second hydrocarbon feedstock, comprising a longer carbon-chain alkane or a longer carbon-chain alkene or both.

Both processes include flowing a feed gas through a heated reaction zone within a reactor and converting an alkane to an alkene or an oxygenate or converting an alkene and an oxygenate to a longer carbon-chain alkene or a longer carbon-chain alkane with or without a solid catalyst at 363-1000 K (e.g., 873 K), preferably at 1-5 atmospheric pressure.

The heated reaction zone is a space or a combination of a space and an inert solid surface. An inert solid surface is the surface of a solid (e.g., a nitric acid washed $SiO_2$ powder) that is inert for an ODH and an OCP reactions relative to a $VO_x/SiO_2$ or $MoO_x/SiO_2$ catalyst.

The feed gas for the ODH process contains an alkane, an oxidizing agent, and a radical initiator. On the other hand, the feed gas for the OCP process contains an alkene, an oxygenate, an oxidizing agent, and a radical initiator.

Examples of the alkane, a required component of the feed gas for the ODH process, include one of $C_{1-20}$ alkanes (e.g., ethane, propane, or heptane) and any combination thereof. The term "alkane" refers to a saturated, linear, or branched hydrocarbon.

Examples of the alkene, a required component of the feed gas for the OCP process include one of $C_{1-20}$ alkenes (e.g., ethylene or propene) and any combination thereof. The term "alkene", a product converted from an alkane, refers to a linear or branched hydrocarbon that contains at least one double bond.

Examples of the oxygenate, a required component of the feed gas for the OCP process, include one of acrolein, acrylic acid, acetic acid, epoxides, aldehydes (e.g., HCHO, $CH_3CHO$, or $C_3H_6O$), glycols, maleic anhydride, and alcohols (e.g., methanol, ethanol, or isopropanol), and any combination thereof.

Examples of the oxidizing agent, another required component of the feed gas for both the ODH and OCP processes, include oxygen, nitrous oxide, and carbon dioxide.

Examples of the radical initiator, yet another required component of the feed gas for both the ODH and OCP processes, include nitric oxide, nitrogen dioxide, halogens, azide compounds, and organic peroxides.

In one embodiment of the ODH or OCP process, the radical initiator is nitric oxide present at 1-500 ppm in the feed gas and the oxidizing agent is oxygen present at 3 kPa-50 kPa in the feed gas.

In another embodiment of the ODH process, the feed gas further contains one or more hydrocarbons other than the alkane, one or more oxygenates, or a combination thereof. For example, a feed gas containing propane, ethylene (i.e., a hydrocarbon other than an alkane), methanol (i.e., an oxygenate), nitric oxide, and oxygen can be subjected to flow through the above-described reaction zone to produce propene.

In still another embodiment of the ODH or OCP process, the feed gas further contains an inert diluent, e.g., helium, nitrogen, carbon dioxide, carbon monoxide, or a combination thereof. Inert diluents can be used to control the concentrations of the reactive components and radical initiators and balance the total pressure of the feed gas.

In a further embodiment of the ODH or OCP process, the feed gas also contains water vapor. Adding water vapor increases the concentration of certain radicals for converting an alkane to an alkene or an alkene and an oxygenate to a longer carbon-chain alkene, thereby improving selectivity in some cases.

The ODH and OCP processes of this invention lead to a high alkene selectivity, e.g., >90%. "Selectivity" respecting a product (i.e., an alkene) is defined as the percentage of the carbon atoms of the reacted alkane or the reacted alkene and oxygenate retained in the product.

The reactor used in the ODH or OCP process of this invention can be, among others, a straight quartz tube, a U-shaped quartz tube, a straight stainless steel tube, and a U-shaped stainless steel tube.

Other features, objects, and advantages of the invention will be apparent from the following drawings and detailed description of several embodiments, and also from the appending claims.

BRIEF DESCRIPTION OF THE DRAWINGS

FIG. 1A is a schematic description of the setup for measuring reaction rates.

FIG. 1B is a photograph of quartz reactors used for the ODH reactions.

FIG. 6A shows $C_3H_8$ conversion to $C_3H_6$ (solid symbols) and $C_2H_4$ (open symbols), as a function of NO pressure at different temperatures (748, 773, and 798 K) in a 12 cm$^3$ quartz reactor (3 kPa $C_2H_6$, 10 kPa $O_2$, and 30 cc/min). Symbol representation: Lozenge, 748 K; triangle, 773 K; and square, 798 K.

FIG. 6B shows $C_3H_6$ (solid symbols) and $C_2H_4$ (open symbols) selectivity during conversion of $C_3H_8$, as a function of NO pressure at different temperatures (748, 773, and 798 K) in a 12 cm$^3$ quartz reactor (3 kPa $C_2H_6$, 10 kPa $O_2$, and 30 cc/min). Symbol representation: Lozenge, 748 K; triangle, 773 K; and square, 798 K.

FIG. 9A shows $C_2H_6$ conversion at 0 (lozenges) or 0.01 kPa (triangles) NO fed to a 12 cm$^3$ quartz reactor (773 K, 10 kPa $O_2$, 30 cc/min).

FIG. 9B shows $C_2H_4$ selectivity during conversion of $C_2H_6$ at 0 (lozenges) or 0.01 kPa (triangles) NO fed to a 12 cm$^3$ quartz reactor (773 K, 10 kPa $O_2$, 30 cc/min).

FIG. 10A shows $C_2H_6$ conversion as a function of $O_2$ pressure selectivity at 0 (lozenges) or 0.01 kPa (triangles) NO fed to a 12 cm$^3$ quartz reactor (773 K, 3 kPa $C_2H_6$, 30 cc/min).

FIG. 10B shows $C_2H_4$ selectivity during conversion of $C_2H_6$ as a function of $O_2$ pressure selectivity at 0 (lozenges) or 0.01 kPa (triangles) NO fed to a 12 cm$^3$ quartz reactor (773 K, 3 kPa $C_2H_6$, 30 cc/min).

FIG. 11A shows $C_2H_6$ conversion as a function of $H_2O$ vapor pressure in a 5.9 cm$^3$ quartz reactor (823 K, 3 kPa $C_2H_6$, 10 kPa $O_2$, 30 cc/min, 0.01 kPa NO).

FIG. 11B shows product selectivity during $C_2H_6$ conversion as a function of $H_2O$ vapor pressure in a 5.9 cm$^3$ quartz reactor (823 K, 3 kPa $C_2H_6$, 10 kPa $O_2$, 30 cc/min, 0.01 kPa NO).

FIG. 17A shows $C_3H_8$ conversion in 6 and 12 $cm^3$ reactors as a function of NO pressure at 30 $cm^3$ $min^{-1}$ flow rate for different residence times in 12 $cm^3$ quartz reactor (773 K, 3 kPa $C_3H_8$, 10 kPa $O_2$, 0-0.03 kPa NO).

FIG. 17B shows alkene selectivity as a function of $C_3H_8$ conversion for different residence times in 12 $cm^3$ quartz reactor (773 K, 3 kPa $C_3H_8$, 10 kPa $O_2$, 0-0.03 kPa NO).

FIG. 20A shows $C_3H_8$ activation rates as a function of $O_2$ pressure at 60 $cm^3$ $min^{-1}$ flow rate and at 773, 788 and 798 K. Dashed curves represent best-fits to the form of Equation 2.

FIG. 20B shows alkene selectivity as a function of conversion for 30-100 $cm^3$ $min^{-1}$ flow rates at 798 K and 1, 3 and 10 kPa $O_2$ (0.005 kPa NO, 3 kPa $C_3H_8$, 12 $cm^3$ reactor). Dashed curves represent best-fits to the form of Equation 2.

FIG. 21A shows $C_3H_8$ activation rates as a function of $C_3H_8$ pressure at 60 $cm^3$ $min^{-1}$ flow rate, 773, 788 and 798. Dashed curves represent best-fits to the form of Equation 2.

FIG. 21B shows alkene selectivity as a function of conversion for 20-150 $cm^3$ $min^{-1}$ at 798 K, 0.6-12 kPa $C_3H_8$ (0.005 kPa NO, 10 kPa $O_2$, 12 $cm^3$ reactor). Dashed curves represent best-fits to the form of Equation 2.

FIG. 24A shows ratios of rate constants $k_2/k_1$ as a function of reciprocal temperature at 0.005 kPa NO, 3 kPa $C_3H_8$, and 10 kPa $O_2$. Dashed lines represent exponential best-fits for the values. Uncertainties represent standard errors.

FIG. 24B shows ratios of rate constants $k_3/k_1$ as a function of reciprocal temperature at 0.005 kPa NO, 3 kPa $C_3H_8$, and 10 kPa $O_2$. Dashed lines represent exponential best-fits for the values. Uncertainties represent standard errors.

DETAILED DESCRIPTION

Figure 2A:
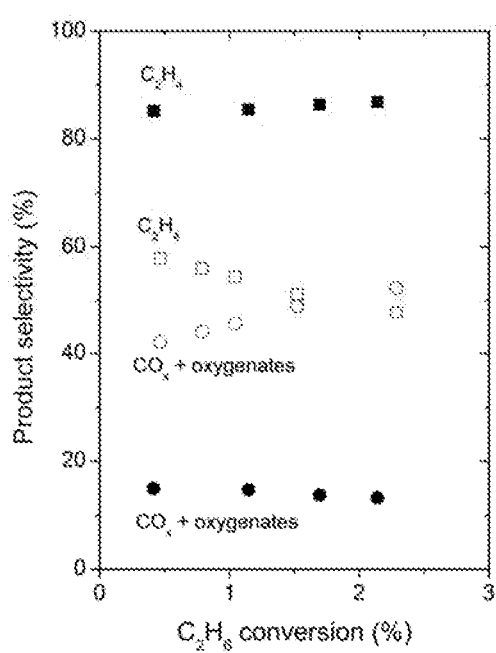
FIG. 2A shows selectivity to $C_2H_6$ oxidation products as a function of $C_2H_6$ conversion in NO promoted homogeneous reactions (solid symbols; 773 K, 0.01 kPa NO, 3 kPa $C_2H_6$, 10 kPa $O_2$, and 12 cm$^3$ reactor) and heterogeneous reactions on 41 wt % $VO_x/SiO_2$ (open symbols; 743 K, 3 kPa $C_2H_6$, and 3 kPa $O_2$).

Described in detail below are gas-phase ODH and OCP processes of the present invention for converting alkanes (e.g., $C_2H_6$ and $C_3H_8$) to alkenes (e.g., $C_2H_4$ and $C_3H_6$) or oxygenates (e.g., methanol, ethanol, isopropanol, or propylene oxide) or converting alkenes (e.g., ethylene and propene) and oxygenates (e.g., methanol, ethanol, isopropanol, or propylene oxide) to longer carbon-chain alkenes, or longer carbon-chain alkanes with or without solid catalysts by contacting alkanes or contacting alkenes and oxygenates with an oxidizing agent (e.g., $O_2$) and a trace amount of a radical initiator (e.g., nitric oxide NO or nitrogen dioxide $NO_2$) in a reactor, with optional addition of water vapor, gaseous diluents (e.g., helium He or nitrogen $N_2$), and inert solids (e.g., nitric acid washed $SiO_2$ powders).

The reaction conditions are optimized to provide high alkane conversion and high alkene selectivity by varying certain parameters such as reaction temperature, concentrations of reactants, and reactor volume.

Only a trace amount of the radical initiator, e.g., 1-500 ppm NO, needs to be present to obtain optimum yields. Unexpectedly, high oxidizing agent concentrations (e.g., 10 kPa-50 kPa $O_2$) lead to better alkene yields, which is counterintuitive and not logically derived from previous studies to minimize $O_2$ in the feed or use non-oxidative processes for such conversions. Indeed, a combination of NO and $O_2$ at optimal concentrations leads to higher production of the specific radicals that perform conversion of an alkane to an alkene or of an alkene and an oxygenate to a longer carbon-chain alkene with excellent selectivity. Of note, NO acts as a radical initiator and may also be considered as a radical as it contains an unpaired electron.

Adding water vapor can also improve the concentration of the specific radicals discussed above, leading to high selectivity and high conversion rate.

Inert diluents can be used to control the concentrations of reactive components and radical initiators. The total pressure of the feed gas is typically 1 atmosphere. If the total pressure of the active components is lower than 1 atmosphere, inert diluents can be added as balance. Further, as pure NO, a radical initiator, is very toxic, its dilution with an inert diluent is preferred.

The ODH process of this invention using propane in a feed gas leads to >80% propylene selectivity and >90% total alkene (propylene+ethylene) selectivity with near 5% propane conversion. Operating near 10% single-pass conversion with recycle results in 80% propylene yield. The yield can be further improved via process optimization.

In one study described below (Example 2), a feed gas including 3 kPa $C_2H_6$, 10 kPa $O_2$, 0.03 kPa NO, and balance He was added to a 12 cm$^3$ reactor maintained at 823 K. >75% $C_2H_6$ conversions and >40% $C_2H_4$ yields were obtained.

In another study described below (Example 3), a feed gas including 3 kPa $C_3H_8$, 10 kPa $O_2$, 0.005 kPa NO, and balance He was added to a 12 cm$^3$ reactor at 773 K. >70% $C_3H_8$ conversions in a single pass through the reactor, >24% $C_3H_6$ yields, and >42% total alkene ($C_2H_4+C_3H_6$) yields were obtained. Extrapolation of conversion studies with variation of temperature and pressures of all reactants and addition of water vapor indicates that much higher conversion rates are achievable.

The present invention provides a cost-effective solution for small scale plants. The ODH and OCP processes of this invention lead to lower costs as much simpler reactors, without movable parts or catalyst regeneration mechanisms, can be used. Indeed, these reactors are much less expensive and easier to handle than catalytic reactors. It can also lead to lower operating costs as (i) exothermic reaction avoids the need for costly external heat, (ii) costs for catalysts and their regeneration can be entirely avoided, and (iii) pumping costs for avoiding pressure drops caused by catalyst beds are lower. These advantages can lead to half the utility cost and much lower effective raw material cost while maintaining similar yields.

The ODH and OCP processes of this invention can play a role in helping mitigate flaring of wet shale gas and wet-natural gas by allowing small-scale economical plants built near their production facilities to better utilize these resources. It can be an effective solution to current bulky large-scale technologies. Regulations on flaring will make such processes more attractive in near future.

Also, the processes can be applied to produce valuable alkenes from other larger hydrocarbons and specialty products with specific alkene isomers, which are in low yield by conventional processes due to their lower thermodynamic stability. Butane, isobutane, hexane, cyclohexane, and methyl cyclohexane all can be used for commercial production of their corresponding alkenes.

When NO is used as a radical initiator, the products of the ODH and OCP processes contain trace amounts of nitrates and other nitrosyl compounds, which can be easily detected using highly sensitive analytical techniques such as infrared spectroscopy and mass spectrometry.

The objective and advantages of the present invention are illustrated in Examples 1-10 below. The following procedures were used for preparing the catalysts and analyzing the data described in the examples.

Vanadium and molybdenum oxides catalysts supported on silica ($VO_x/SiO_2$, $MoO_x/SiO_2$) were prepared by wet impregnation of ammonium metavanadate and ammonium helptamolybdate precursors (Sigma Aldrich), respectively, on $SiO_2$ powders (Sigma Aldrich).

ODH reactions were carried out at near-atmospheric pressures (101.3 kPa) in a U-shaped quartz tube (¼" OD) with a bulb and a quartz frit designed for holding inert or catalytic solids during the flow of gaseous reactants (FIG. 1). The reactor, either empty or filled with solids, was heated using a resistively heated furnace (National Element). The temperature was measured using a K-type thermocouple (Omega) placed within dimple at the reactor wall and controlled using temperature controller (Watlow). Reactant mixtures contained $C_2H_6$ or $C_3H_8$ (99.9%, Airgas), $O_2$ (99.999%, Airgas), He (99.999%, Airgas), NO (99.9%, Airgas) and $H_2O$ (deionized). Electronic mass flow controllers (Parker) were used to supply reactant and diluent gases and NO. $H_2O$ was evaporated into flowing alkane/$O_2$/NO/He stream using a liquid syringe pump (Cole Parmer, Model No. 100). The concentrations of the reactants and products were measured by a gas chromatograph (Agilent 7890B) equipped with a flame ionization detector (FID) and a thermal conductivity detector (TCD). Hydrocarbons (i.e., $C_2H_6$, $C_2H_4$, $C_3H_8$, and $C_3H_6$) and oxygenates other than HCHO (i.e., $CH_3CHO$ and $C_3H_6O$) were separated using HP-PLOT Q capillary column (30 mm×0.32 mm×20.00 μm) and detected with FID. $O_2$, CO, $CO_2$ and HCHO were separated using Carboxen-1000 packed column (10'⅛" 2 mm 60/80 mesh) and detected using the TCD. Calibration curves were created using reactants and expected products within the range of experimental concentrations. All transfer lines were kept above 363 K to avoid condensation of reactants and products.

The term "conversion", "selectivity", "yield", and "residence time" are used to describe the results of reactions and performance of the processes described in the examples below. "Conversion" refers to the percentage of the fed alkane or fed alkene and oxygenate converted to products at the reactor effluent. "Selectivity" for a product (e.g., $C_2H_4$, $C_3H_6$, CO, or $CO_2$) is defined as the percentage of the carbon atoms of the reacted alkane or reacted alkene and oxygenate retained in that specific product. "Yield" of a specific product reflects the multiplication of alkane conversion or alkene and oxygenate conversion and selectivity for that product. "Residence time" of a species represents the reactor volume (in m$^3$) divided by the moles of that species fed per second to the reactor.

Without further elaboration, it is believed that one skilled in the art can, based on the above description, utilize the present invention to its fullest extent. The specific embodiments described in Examples 1-15 below are, therefore, to be construed as merely illustrative, and not limitative of the remainder of the disclosure in any way whatsoever. All publications cited herein are incorporated by reference.

In one aspect, provided are gas-phase oxidative dehydrogenation (ODH) processes for converting an alkane to an alkene or an oxygenate, comprising:

flowing a feed gas through a heated reaction zone within a reactor, wherein the feed gas comprises an alkane, an oxidizing agent, and a radical initiator, wherein:

the heated reaction zone has a temperature of about 363 to about 1000 K; and the heated reaction zone is a space or a combination of a space and an inert solid surface.

In certain embodiments, the alkane is a $C_{1-20}$ alkane.

In certain embodiments, the alkane is ethane or propane.

In certain embodiments, the oxidizing agent is oxygen, nitrous oxide, or carbon dioxide.

In certain embodiments, the oxidizing agent is oxygen.

In certain embodiments, oxygen is present at about 3 kPa to about 50 kPa in the feed gas.

In certain embodiments, the radical initiator is nitric oxide, nitrogen dioxide, a halogen, an azide compound, or organic peroxide.

In certain embodiments, the radical initiator is nitric oxide or nitrogen dioxide.

In certain embodiments, the radical initiator is nitric oxide present at about 1 to about 500 ppm in the feed gas.

In certain embodiments, the feed gas further comprises one or more hydrocarbons.

In certain embodiments, the feed gas further comprises an inert diluent.

In certain embodiments, the inert diluent is helium, nitrogen, carbon dioxide or carbon monoxide.

In certain embodiments, the inert diluent is helium or nitrogen.

In certain embodiments, the feed gas further comprises water vapor.

In certain embodiments, the process is performed at about 1 to about 5 atmospheric pressure.

In certain embodiments, the process is performed at about 1 atmospheric pressure.

In certain embodiments, the heated reaction zone has a temperature of about 363 to about 873 K.

In certain embodiments, the process is performed in the absence of a solid catalyst.

In certain embodiments, the process is performed with the presence of a solid catalyst.

In certain embodiments, the solid catalyst is $VO_x/SiO_2$.

In certain embodiments, the solid catalyst is used at an amount of about 20 wt % to about 60 wt %.

In certain embodiments, the solid catalyst is used at an amount of about 40 wt %.

In certain embodiments, the alkane is propane, the oxidizing agent is oxygen, the radical initiator is nitric oxide or nitrogen dioxide.

In certain embodiments, the alkene formed is ethylene or propylene.

In certain embodiments, the oxygenate formed is propylene oxide.

In certain embodiments, the reactor is a straight quartz tube, a U-shaped quartz tube, a straight stainless steel tube, or a U-shaped stainless steel tube.

In certain embodiments, the reactor is a U-shaped quartz tube.

In another aspect, provided are gas-phase coupling processes for converting a hydrocarbon feedstock to an effluent stream, comprising:

flowing a feed gas comprising a hydrocarbon feedstock, an oxidizing agent, and a radical initiator through a heated reaction zone within a reactor;

wherein:

the hydrocarbon feedstock comprises an oxygenate, and a $C_1$-$C_6$ alkane or a $C_2$-$C_6$ alkene;

the effluent stream comprises a $C_7$-$C_{20}$ alkane or a $C_7$-$C_{20}$ alkene or both;

the heated reaction zone has a temperature of about 363 to about 1000 K; and the heated reaction zone is a space or a combination of a space and an inert solid surface, whereby the effluent stream is produced.

In yet another aspect, provided are gas-phase coupling processes for converting an alkene and an oxygenate to a longer carbon-chain alkene or a longer carbon-chain alkane, comprising:

flowing a feed gas through a heated reaction zone within a reactor, wherein the feed gas comprises an alkene, an oxygenate, an oxidizing agent, and a radical initiator, wherein:

the heated reaction zone has a temperature of about 363 to about 1000 K; and the heated reaction zone is a space or a combination of a space and an inert solid surface.

In certain embodiments, the alkene in the feed gas comprises a $C_{2-20}$ alkene.

In certain embodiments, the alkene in the feed gas comprises a $C_{2-6}$ alkene.

In certain embodiments, the alkene in the feed gas comprises ethylene.

In certain embodiments, the oxygenate in the feed gas comprises $C_{1-6}$ alcohol.

In certain embodiments, the oxygenate in the feed gas comprises methanol, ethanol or isopropanol.

In certain embodiments, the oxidizing agent is oxygen.

In certain embodiments, the oxygen is present at about 3 kPa to about 50 kPa in the feed gas.

In certain embodiments, the radical initiator is nitric oxide present at about 1 to about 500 ppm in the feed gas.

In certain embodiments, the feed gas further includes an inert diluent.

In certain embodiments, the inert diluent is helium, nitrogen, carbon dioxide, or carbon monoxide.

In certain embodiments, the inert diluent is helium or nitrogen.

In certain embodiments, the feed gas further comprises water vapor.

In certain embodiments, the process is performed at about 1 to about 5 atmospheric pressure.

In certain embodiments, the process is performed at about 1 atmospheric pressure.

In certain embodiments, the process is performed at a temperature from 363-873 K.

In certain embodiments, the process is performed in the absence of a solid catalyst.

In certain embodiments, the lower alkene is propene or ethylene, the oxygenate is methanol, the oxidizing agent is oxygen, and the radical initiator is nitric oxide or nitrogen dioxide.

In certain embodiments, the reactor is a straight quartz tube, a U-shaped quartz tube, a straight stainless steel tube, or a U-shaped stainless steel tube.

In certain embodiments, the reactor is a U-shaped quartz tube.

Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that, the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), ten-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include w-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), i-Pr (—$CH(CH_3)_2$), n-Pr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include hut are not limited to, substituted methylene (—$CH(CH_3)$—, (—$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance front 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH=CH—) and propenylene (e.g., —CH=CHCH_2—, —CH_2—CH=CH—). Exemplary substituted alkenylene groups, e.g., substituted with one or more alkyl (methyl) groups, include but are not limited to, substituted ethylene (—$C(CH_3)$=CH—, —CH=C(CH_3)—), substituted propylene (e.g., —$C(CH_3)$=CHCH_2—, —CH=C(CH_3)CH_2—, —CH=CHCH(CH_3)—, —CH=CHC(CH_3)_2—, —CH(CH_3)—CH=CH—, —C(CH_3)_2—CH=CH—, —CH_2—C(CH_3)=CH—, —CH_2—CH=(CH_3)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon tuple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and/or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group Is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and 1 or 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and 1 or 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the and group is unsubstituted C$_{6-14}$ aryl. In certain embodiments, the aryl group is substituted C$_{6-14}$ aryl.

In certain embodiments, an aryl group substituted with one or more of groups selected from halo, C$_{1-8}$ alkyl, C$_{1-8}$ haloalkyl, cyano, hydroxy, C$_{1-8}$ alkoxy, and amino.

Examples of representative substituted aryls include the following

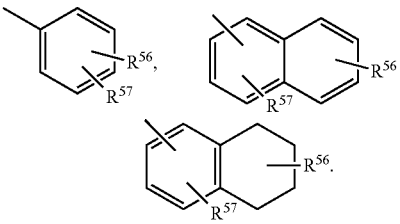

wherein one of R$^{56}$ and R$^{57}$ may be hydrogen and at least one of R$^{56}$ and R$^{57}$ is each independently selected from C$_{1-8}$ alkyl, C$_{1-8}$ haloalkyl, 4- to 10-membered heterocyclyl, alkanoyl, C$_{1-8}$ alkoxy, heteroaryl oxy, alkyl amino, arylamino, heteroaryl amino, NR$^{58}$COR$^{59}$, NR$^{58}$SOR$^{59}$NR$^{58}$SO$_2$R$^{59}$, COOalkyl, COGaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_{1-8}$ alkyl, C$_{1-4}$ haloalkyl, C$_{3-10}$ carbocyclyl, 4- to 10-membered heterocyclyl, C$_{6-10}$ aryl, substituted C$_{6-10}$ aryl, 5-10 membered heteroaryl, or substituted 5- to 10-membered heteroaryl.

Other representative aryl groups having a fused heterocycyl group include the following:

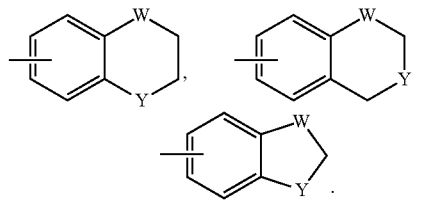

wherein each W is selected from C(R$^{66}$)$_2$, NR$^{66}$, O, and S; and each Y is selected from carbonyl, NR$^{66}$, O and S; and R$^{66}$ is independently hydrogen, C$_{1-8}$ alkyl, C$_{3-10}$ carbocyclyl, 4- to 10-membered heterocycyl, C$_{6-10}$ aryl, and 5- to 10-membered heteroaryl.

"Fused aryl" refers to an aryl having two of its ring carbon in common with a second aryl or heteroaryl ring or with a carbocyclyl or heterocycyl ring.

"Aralkyl" is a subset of alkyl and aryl, as defined herein, and refers to an optionally substituted alkyl group substituted by an optionally substituted aryl group.

"Heteroaryl" refers to a radical of a 5- to 10-membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5- to 10-membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with, one or more carbocyclyl or heterocycyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined, above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5- to 10-membered aromatic ring system having ring carbon atoms and 1-4 ring heteroatoms provided in the aromatic ring system, wherein each heteroatom is independently selected from nitrogen, oxygen, and sulfur ("5- to 10-membered heteroaryl"). In some embodiments, a heteroaryl group is a 5- to 8-membered aromatic ring system having ring carbon atoms and 1-4 ring heteroatoms provided in the aromatic ring system, wherein each heteroatom is independently selected from nitrogen, oxygen, and sulfur ("5- to 8-membered heteroaryl"). In some embodiments, a heteroaryl group is a 5- to 6-membered aromatic ring system having ring carbon atoms and 1-4 ring heteroatoms provided in the aromatic ring system, wherein each heteroatom is independently selected from nitrogen, oxygen, and sulfur ("5- to 6-membered heteroaryl"). In some embodiments, the 5-6 membered heteroaryl has 1-3 ring heteroatoms selected from nitrogen, oxygen, and sulfur. In some embodiments, the 5- to 6-membered heteroaryl has 1-2 ring heteroatoms selected from nitrogen, oxygen, and sulfur. In some embodiments, the 5- to 6-membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5- to 14-membered heteroaryl. In certain embodiments, the heteroaryl group is substituted 5- to 14-membered heteroaryl.

Exemplary 5-membered heteroaryl groups containing one heteroatom include, without limitation, pyrroyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups Include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

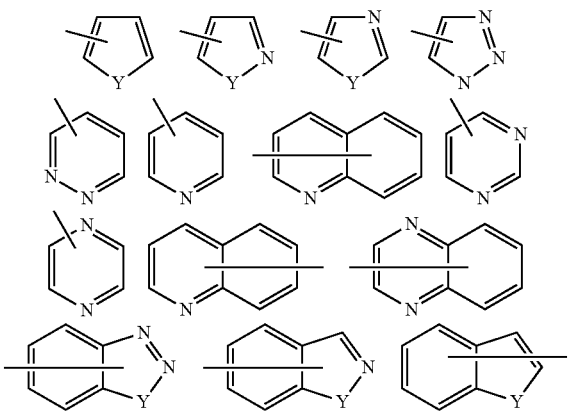

wherein each Y is selected from carbonyl, N, NR$^{65}$, O, and S; and R$^{65}$ is independently hydrogen, C$_{1-8}$ alkyl, C$_{3-10}$ carbocyclyl, 4-10 membered heterocyclyl, C$_{6-10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the nonaromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-5}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more and or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Examples of $C_{5-6}$ carbocyclyl groups include cyclopentyl ($C_5$) and cyclohexyl ($C_6$). Examples of $C_{3-6}$ carbocyclyl groups include the aforementioned $C_{5-6}$ carbocyclyl groups as well as cyclopropyl ($C_3$) and cyclobutyl ($C_4$). Examples of $C_{3-8}$ carbocyclyl groups include the aforementioned $C_{3-6}$ carbocyclyl groups as well as cycloheptyl ($C_7$) and cyclooctyl ($C_8$). Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

"Heterocyclyl" or "heterocyclic" refers to a radical of a 3- to 10-membered non-aromatic-ring system having ring carbon atoms and 1 to 4 ring heteroatoms, wherein each heteroatom is independently selected from nitrogen, oxygen, sulfur, boron, phosphorus, and silicon ("3- to 10-membered heterocyclyl"). In heterocyclyl groups that contain one or more nitrogen atoms, the point of attachment cart be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and cart be saturated or can be partially unsaturated. Heterocyclyl bicyclic ring systems can include one or more heteroatoms in one or both rings. "Heterocyclyi" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3- to 10-membered heterocyclyl. In certain embodiments, the heterocyclyl group is substituted 3- to 10-membered heterocyclyl.

In some embodiments, a heterocyclyl group is a 5- to 10-membered non-aromatic ring system having ring carbon atoms and 1-4 ring heteroatoms, wherein each heteroatom is independently selected from nitrogen, oxygen, sulfur, boron, phosphorus, and silicon ("5- to 10-membered heterocyclyl"). In some embodiments, a heterocyclyl group is a 5- to 8-membered non-aromatic ring system having ring carbon atoms and 1-4 ring heteroatoms, wherein each heteroatom is independently selected from nitrogen, oxygen, and sulfur ("5- to 8-membered heterocyclyl"). In some embodiments, a heterocyclyl group is a 5- to 6-membered non-aromatic ring system having ring carbon atoms and 1-4 ring heteroatoms, wherein each heteroatom is independently selected from nitrogen, oxygen, and sulfur ("5- to 6-membered heterocyclyl"). In some embodiments, the 5-6 membered heterocyclyl has 1-3 ring heteroatoms selected from nitrogen, oxygen, and sulfur. In some embodiments, the 5- to 6-membered heterocyclyl has 1-2 ring heteroatoms selected from nitrogen, oxygen, and sulfur, fir some embodiments, the 5- to 6-membered heterocyclyl has one ring heteroatom selected from nitrogen, oxygen, and sulfur.

Exemplary 3-membered heterocyclyl groups containing one heteroatom include, without limitation, aziridinyl, oxiranyl, thiorenyl. Exemplary 4-membered heterocyclyl groups containing one heteroatom include, without limitation, azetidinyl, oxetanyl and thietanyl. Exemplary 5 membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

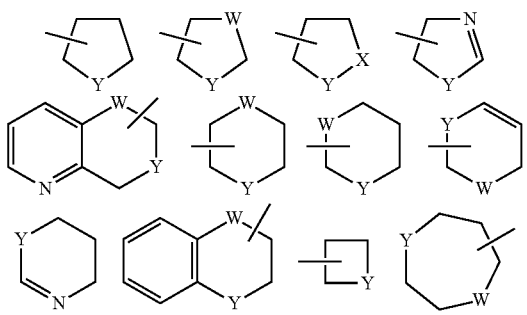

-continued

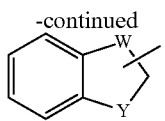

wherein each W is selected from $CR^{67}$, $C(R^{67})_2$, $NR^{67}$, O, and S; and each Y is selected from $NR^{67}$, O, and S; and $R^{67}$ is independently hydrogen, $C_{1-8}$ alkyl, $C_{3-10}$ carbocyclyl, 4- to 10-membered heterocyclyl, $C_{6-10}$ aryl, 5- to 10-membered heteroaryl. These heterocyclyl rings may be optionally substituted with one or more groups selected from the group consisting of acyl acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, carbocyclyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen or sulfur heteroatom. Hetero may be applied to any of the hydrocarbyl groups described above such as alkyl, e.g., heteroalkyl, carbocyclyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_{1-8}$ alkyl, —C(O)—(CH$_2$)$_t$(C$_{6-10}$ and), —C(O)—(CH$_2$)$_t$(5-to 10-membered heteroaryl), —C(O)—(CH$_2$)$_t$(C$_{3-10}$ carbocyclyl), and —C(O)—(CH$_2$)$_t$(4- to 10-membered heterocyclyl), wherein t is an integer from 0 to 4. In certain embodiments, R is $C_{1-8}$ alkyl, substituted with halo or hydroxy; or $C_{3-10}$ carbocyclyl, 4- to 10-membered heterocyclyl, $C_{6-10}$ aryl, arylalkyl, 5- to 10-membered heteroaryl or heteroaryl alkyl, each of which is substituted with unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy.

"Acylamino" refers to a radical —$NR^{22}C(O)R^{23}$, where each instance of $R^{22}$ and $R^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}$C(O)—C$_{1-8}$ alkyl, —$NR^{24}$C(O)—(CH$_2$)$_t$(C$_{6-10}$ aryl), —$NR^{24}$C(O)—(CH$_2$)$_t$(5- to 10-membered heteroaryl), —$NR^{24}$C(O)—(CH$_2$)$_t$(C$_{3-10}$ carbocyclyl), and —$NR^{24}$C(O)—(CH$_2$)$_t$(4- to 10-membered heterocyclyl), wherein t is an integer from 0 to 4, and each $R^{24}$ independently represents H or $C_{1-8}$ alkyl. In certain embodiments, $R^{25}$ is H, $C_{1-8}$ alkyl, substituted with halo or hydroxy; $C_{3-10}$ carbocyclyl, 4- to 10-membered heterocyclyl, $C_{6-10}$ aryl, arylalkyl, 5-10 membered heteroaryl or heteroarylalkyl, each of which is substituted with unsubstituted $C_{1-4}$ alkyl, halo, unsubstituted $C_{1-4}$ alkoxy, unsubstituted $C_{1-4}$ haloalkyl, un substituted $C_{1-4}$ hydroxy alkyl, or unsubstituted $C_{1-4}$ haloalkoxy or hydroxy; and $R^{26}$ is H, $C_{1-8}$ alkyl, substituted with halo or hydroxy; $C_{3-10}$ carbocyclyl, 4-10 membered heterocyclyl, $C_{6-10}$ aryl, arylalkyl, 5-10 membered heteroaryl or heteroarylalkyl, each of which is substituted with unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxyl; provided at least one of $R^{25}$ and $R^{26}$ is other than H.

"Acyloxy" refers to a radical —OC(O)$R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_{1-8}$ alkyl, substituted with halo or hydroxy; $C_{3-10}$ carbocyclyl, 4- to 10-membered heterocyclyl, $C_{6-10}$ aryl, arylalkyl, 5- to 10-membered heteroaryl or heteroarylalkyl, each of which is substituted with unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy.

"Alkoxy" refers to the group —OR$^{29}$ where $R^{25}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_{6-10}$ aryl, aryloxy, carboxyl, cyano, $C_{3-10}$ carbocyclyl, 3- to 10-membered heterocyclyl, halogen, 5- to 10-membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, hut are not limited to, —O—(CH$_2$)$_t$(C$_{6-10}$ aryl), —O—(CH$_2$)$_t$(5- to 10-membered heteroaryl), —O—(CH$_2$)$_t$(C$_{3-10}$ carbocyclyl), and —O—(CH$_2$)$_t$(4- to 10-membered heterocyclyl), wherein t is an integer from 0 to 4 and any aryl, heteroaryl, carbocyclyl or heterocyclyl groups present, may themselves be substituted by unsubstituted $C_{1-4}$ alkyl, halo, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy. Particular exemplary 'substituted alkoxy' groups are —OCF$_3$, —OCH$_2$CF$_3$, —OCH$_2$Ph, —OCH$_2$— cyclopropyl, —OCH$_2$CH$_2$OH, and —OCH$_2$CH$_2$NMe$_2$.

These and other exemplary substituents are described in more detail in the Detailed Description, Examples, and claims. The invention is not intended to be limited in any manner by the above exemplary listing of substituents.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Figure 2B:
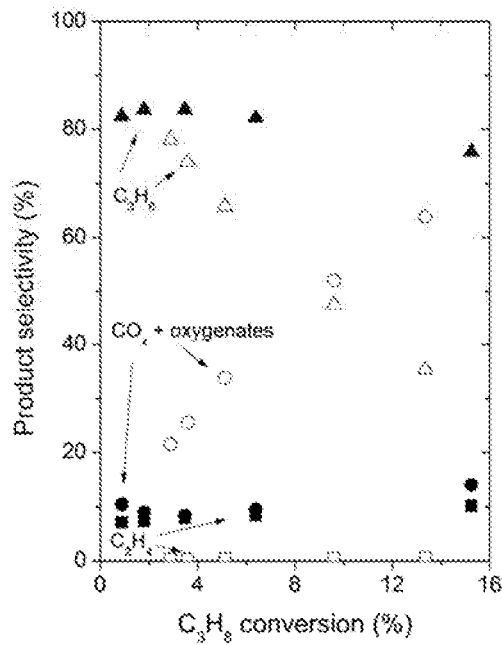
FIG. 2B shows selectivity to $C_3H_8$ oxidation products as a function of $C_3H_8$ conversion in NO promoted homogeneous reactions (solid symbols; 748 K, 0.01 kPa NO, 3 kPa $C_3H_8$, 10 kPa $O_2$, 3 kPa $H_2O$, and 12 cm$^3$ reactor) and heterogeneous reactions on 41 wt % $VO_x/SiO_2$ (open symbols; 773 K, 3 kPa $C_3H_8$, and 3 kPa $O_2$). Symbol representation: Trialgle, $C_3H_8$; squares, $C_2H_4$; circle, $CO_x$ and oxygenates (HCHO, $CH_3CHO$).

Example 1: Comparison of Heterogeneous $C_2H_6$ and $C_3H_8$ Oxidations to Respective Homogeneous Reactions FIGS. 2A-2B show the effect of alkane conversions on selectivity to products of $C_2H_6$ (FIG. 2A) and $C_3H_8$ (FIG. 2B) oxidation reactions on $VO_x/SiO_2$ catalyst held within a quartz reactor without NO feed (heterogeneous reaction on a representative selective ODH catalyst) and in an empty reactor with 0.01 kPa NO (homogeneous reaction) at same feed concentrations of $C_2H_6$ or $C_3H_8$ and $O_2$, and similar temperatures and range of conversions achieved by varying the total flowrate of feed gas mixture (12-120 cc/min).

At 1% $C_2H_6$ conversion, the homogeneous reactions show much higher selectivity to $C_2H_4$ than their heterogeneous counterpart (85% versus 50%, respectively; FIG. 2A), which confirms the potential of NO or $NO_2$ radical-initiator-based homogeneous ODH process to be efficient and selective. Furthermore, the $C_2H_4$ selectivity in heterogeneous reactions decreases sharply with increasing conversion, in contrast to the homogeneous experiment that shows a nearly constant selectivity around 85% for the entire conversion range, thus confirming that high selectivity at high conversion can be achieved to obtain improved $C_2H_4$ yield.

The $C_3H_6$ oxidation reactions (FIG. 2B) show similar trends as the $C_2H_4$ reactions. The $C_3H_6$ selectivity at a given conversion is lower in heterogeneous reactions than in the homogeneous counterparts. Other products obtained in homogeneous reactions include significant amounts of $C_2H_4$, which is another useful product. In contrast, the heterogeneous reactions produced virtually no $C_2H_4$ and much higher CO, $CO_2$ and oxygenates than the homogeneous reactions. As is the case of $C_2H_6$ reactions, the selectivity to alkenes decreases with conversion much more rapidly in heterogeneous reactions than in heterogeneous reactions. Thus, chemical processes based on homogeneous gas-phase alkane-$O_2$—NO reactions can provide high selectivity and yield to alkene products, an approach, shown here for $C_2H_6$ and $C_3H_8$ alkanes as specific examples, which may be applied to other alkanes, cycloalkanes and aromatic hydrocarbons and oxygenates in reactions that involves removal of hydrogen from carbon atoms.

Figure 3A:
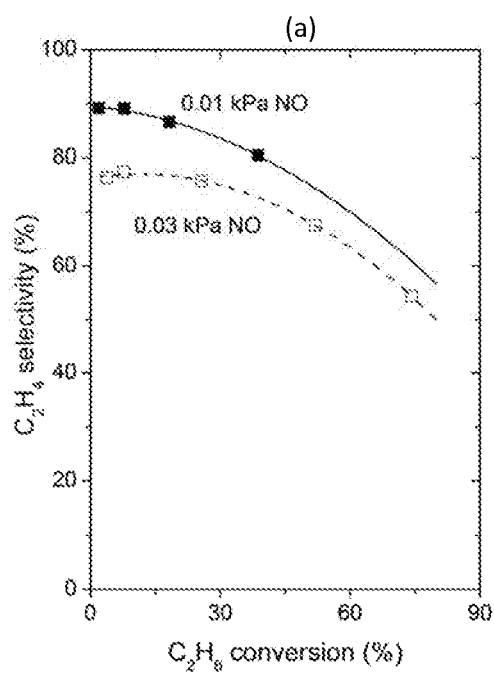
FIG. 3A shows measured $C_2H_4$ selectivity as a function of $C_2H_6$ conversion at 0.01 and 0.03 kPa NO in the feed gas in a 12 cm$^3$ empty quartz reactor (823 K, 3 kPa $C_2H_6$, and 10 kPa $O_2$). The solid and dashed curves represent best second order polynomial fits.
Figure 3B:
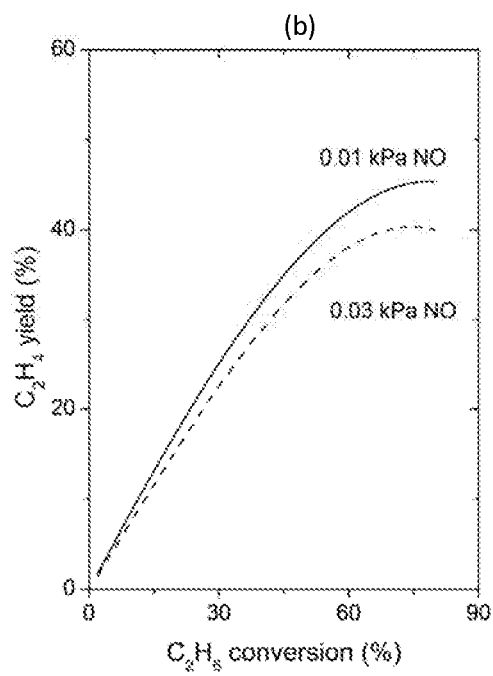
FIG. 3B shows measured $C_2H_4$ yield as a function of $C_2H_6$ conversion at 0.01 and 0.03 kPa NO in the feed gas in a 12 cm$^3$ empty quartz reactor (823 K, 3 kPa $C_2H_6$, and 10 kPa $O_2$). The solid and dashed curves represent yields (=conversion×selectivity) predicted from these fits.

Example 2: $C_2H_6$ Conversion and $C_2H_4$ Selectivity and Yield in Homogeneous Reactions When the flow rate (space velocity) of the $C_2H_6$—$O_2$—NO mixture with given feed concentration is decreased, the residence time on the gases increases and leads to higher $C_2H_6$ conversion. FIGS. 3A-3B show the effect of conversion change via residence time variation on the selectivity and yield of $C_2H_4$ at two different NO feed concentrations (823 K, 3 kPa $C_2H_6$, 10 kPa $O_2$; 0.01 and 0.03 kPa NO). The 0.01 kPa NO feed led to the highest attainable conversion of 38% at 20 cc/min flow rate, while the 0.03 kPa NO led to 76% conversion at the same flow rate. The $C_2H_4$ selectivity decreases with increasing $C_2H_6$ conversion and, at a given conversion, its value is at 0.01 kPa NO feed is higher than the value at 0.03 kPa NO feed, suggesting that higher NO concentration increases reaction rates but also causes a slight decrease in selectivity. These conversion and selectivity data lead to a maximum $C_2H_4$ yield of 40% at 0.03 kPa NO and an extrapolated attainable yield of 45% at 0.01 kPa NO.

Figure 4A:
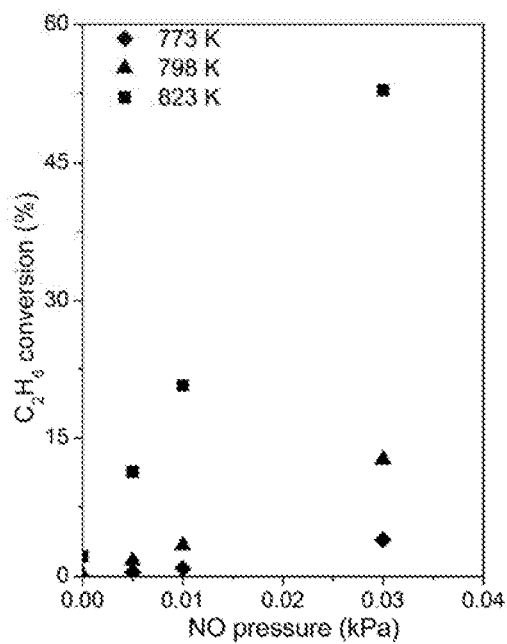
FIG. 4A shows $C_2H_6$ conversion to $C_2H_4$ (solid symbols) and other products (open symbols; $CO+CO_2+CH_3CHO+HCHO$), as a function of NO pressure at different temperatures (773, 798 and 823 K) in a 12 cm$^3$ quartz reactor (3 kPa $C_2H_6$, 10 kPa $O_2$, and 30 cc/min). Symbol representation: Lozenge, 773 K; triangle, 798 K; and square, 823 K.
Figure 4B:
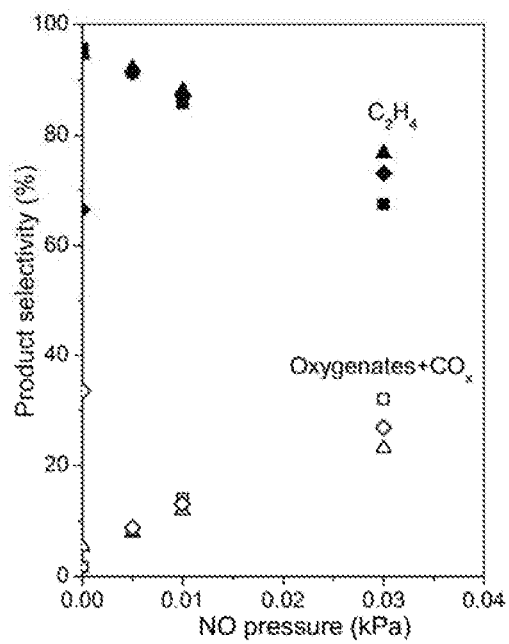
FIG. 4B shows $C_2H_4$ selectivity (solid symbols) among other products (open symbols; $CO+CO_2+CH_3CHO+HCHO$) as a function of NO pressure at different temperatures (773, 798 and 823 K) in a 12 cm$^3$ quartz reactor (3 kPa $C_2H_6$, 10 kPa $O_2$, and 30 cc/min). Symbol representation: Lozenge, 773 K; triangle, 798 K; and square, 823 K.

FIGS. 4A-4B show the effect of NO pressure (0-0.03 kPa) on $C_2H_6$ conversion and selectivity to oxidation products at different temperatures (773, 798 and 823 K; 3 kPa $C_2H_6$, 10 kPa $O_2$, 30 c/min). $C_2H_6$ conversion increases sharply with increasing NO pressures and is higher at higher temperatures. The conversion at the smallest NO feed (0.005 kPa, FIG. 4A), is at least 5, 10 and 21 times higher than the conversions in NO free feeds at 823, 798 and 773 K, respectively. These data show that even a trace concentration of NO can cause a marked increase in alkane conversion, and therefore, NO plays an important role in carrying out homogeneous oxidative dehydrogenation reactions. $C_2H_4$ selectivity decreases with increasing NO pressure (FIG. 4B), which reflects a combined effect of increased conversion and the role of higher NO in decreasing selectivity (as shown in FIGS. 3A-3B). Higher temperatures lead to similar $C_2H_4$ selectivity as lower temperature values, in spite of the much higher conversions, suggesting that the attainable $C_2H_4$ yields given by the product of conversion and selectivity increases with temperature.

Along with the major product $C_2H_4$, small amounts of HCHO, $CH_3CHO$, CO and $CO_2$ are detected in the product stream as shown in FIG. 4B. Some of the following examples show only alkene selectivity and those cases it is implied that the difference between 100% and the reported alkene selectivity corresponds to these oxygenate and $CO_x$ products or trace amounts (<0.4%) or $CH_4$.

These results show that >40% yields of $C_2H_4$ were obtained on our experiments and further improvements can be made by varying NO pressure, temperature and flow rates. The next example shows similar the conversion-selectivity-yield relations for NO promoted homogeneous gas-phase $C_3H_8$ oxidation reactions. Subsequently, other factors affecting the attainable yields and the design of optimum homogeneous processes are discussed.

Figure 5A:
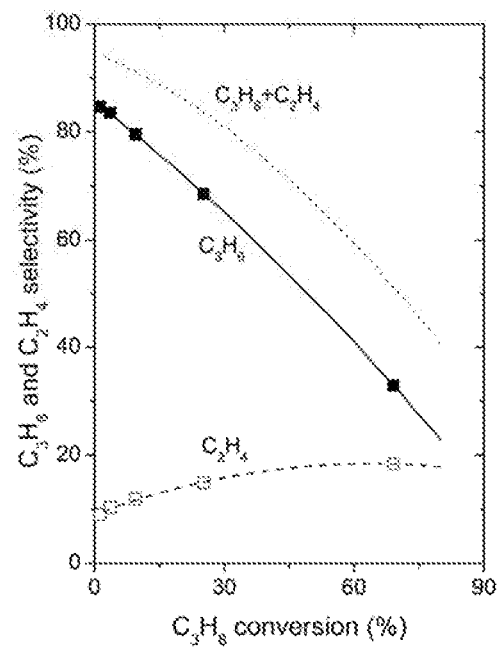
FIG. 5A shows measured $C_3H_6$ (solid symbols) and $C_2H_4$ (open symbols) selectivity as a function of $C_3H_8$ conversion at 0.005 kPa NO in the feed gas in a 12 cm$^3$ empty quartz reactor (773 K, 3 kPa $C_3H_8$, 10 kPa $O_2$, and 3 kPa $H_2O$). The solid and dashed curves represent best second order polynomial fits predicted from these fits. The dotted curves represent summation of values predicted for $C_3H_6$ and $C_2H_4$.
Figure 5B:
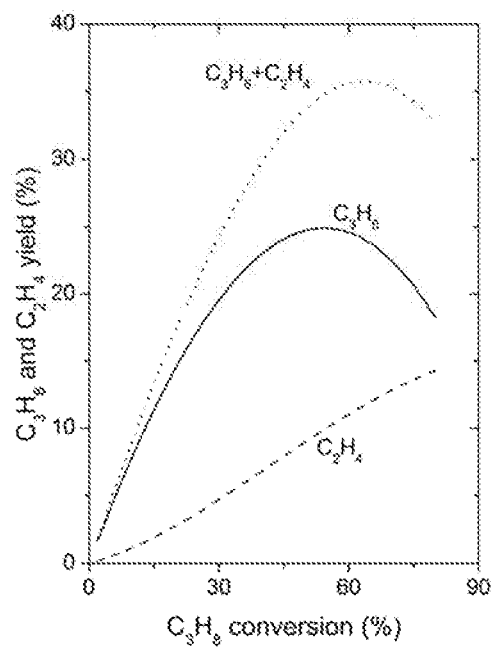
FIG. 5B shows measured respective yields of $C_3H_6$ (solid symbols) and $C_2H_4$ (open symbols), as a function of $C_3H_8$ conversion at 0.005 kPa NO in the feed gas in a 12 cm$^3$ empty quartz reactor (773 K, 3 kPa $C_3H_8$, 10 kPa $O_2$, and 3 kPa $H_2O$). The solid and dashed curves represent yields (=conversion×selectivity) predicted from these fits. The dotted curves represent summation of values predicted for $C_3H_6$ and $C_2H_4$.

Example 3: $C_3H_8$ Conversion and Alkene ($C_3H_6$, $C_2H_4$) Selectivity and Yield in Homogeneous Reactions FIGS. 5A-5B show the effect of conversion change via residence time variation on the selectivity and yield of $C_3H_6$ and $C_2H_4$ (773 K, 0.01 kPa NO, 3 kPa $C_3H_8$, 10 kPa $O_2$, 3 kPa $H_2O$). The $C_3H_6$ selectivity decreases significantly (85% to 33%) while the $C_2H_4$ selectivity increases slightly (9% to 18%) with increasing conversion (0-69%). These conversion and selectivity data lead to a maximum $C_3H_6$ yield of 25% and $C_2H_4$ yields up to 15%, with maximum alkene ($C_3H_6$+$C_2H_4$) yields >35%.

FIGS. 6A-7B show the effect of NO pressure (0-0.03 kPa) on $C_3H_8$ conversion and selectivity to $C_3H_8$ and $C_2H_4$ at different temperatures (748, 773 and 798 K; 3 kPa $C_2H_6$, 10 kPa $O_2$, 30 c/min). $C_3H_8$ conversion increases sharply with increasing NO pressures and is higher at higher temperatures (FIG. 6A), as in the case of $C_2H_6$ shown in FIGS. 4A-4B. The $C_3H_6$ selectivity decreases, and the $C_2H_4$ selectivity increases, with increasing NO pressure (FIG. 4B). These trends reflect a combined effect of increased conversion and the possible role of NO pressure on selectivity at same conversion. Higher temperatures lead to higher or similar $C_3H_6$ selectivity (FIG. 6B), and higher $C_3H_8$ conversions (FIG. 6A), at same NO pressure, suggesting that the attainable $C_3H_6$ yields given by the product of conversion and selectivity increases markedly with temperature.

Thus, simple moderate temperature processes with yields relevant to practical alkane dehydrogenation process are achievable in NO promoted homogeneous gas-phase oxidation processes, which can be improved further by optimizing reaction conditions. Next, we change different process conditions to assess their impacts on the performances. In particular, it is shown that (i) temperature increases and $H_2O$ co-feeds can improve conversion and selectivity and (ii) Increasing alkane and $O_2$ pressure retains the high conversion and selectivity and improves it to some extent suggesting the applicability of this process even in denser reactant feeds for more practical processes. In many cases, where only the results of $C_2H_6$ reactions are shown, $C_3H_8$ reactions were also performed and showed analogous effects.

Example 4: Effect of Reactor Volume on Alkane Conversion and Alkene Selectivity

Figure 7A:
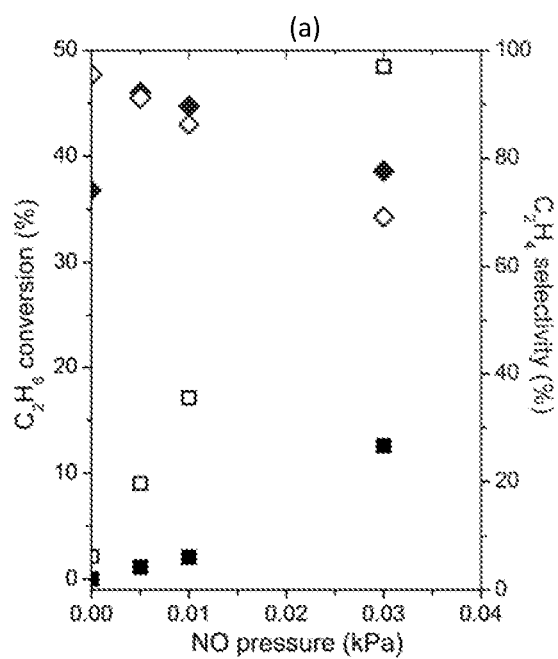
FIG. 7A shows $C_2H_6$ conversion (squares) and $C_2H_4$ selectivity (lozenges) (3 kPa $C_2H_6$, 10 kPa $O_2$, 30 cc/min, and 823 K) as a function of NO pressure fed to 5.9 cm$^3$ (solid symbols) and 12 cm$^3$ (hollow symbols) quartz reactors.
Figure 7B:
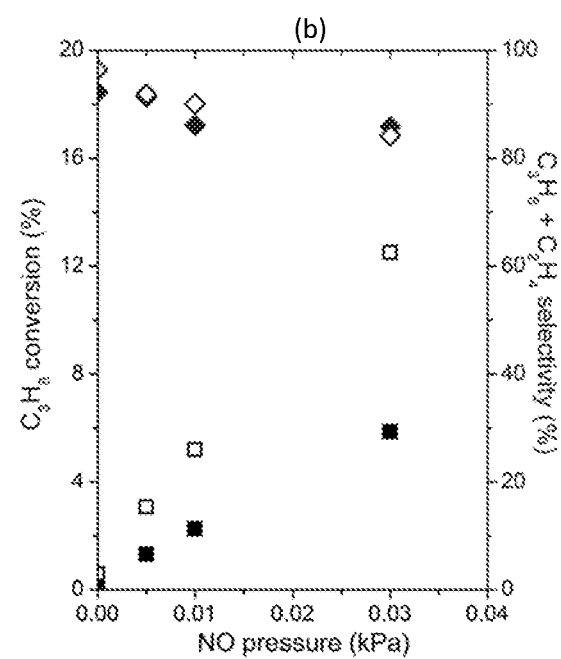
FIG. 7B shows $C_3H_8$ conversion (squares) and alkene selectivity ($C_3H_6+C_2H_4$, lozenges) (3 kPa $C_3H_8$, 10 kPa $O_2$, 30 cc/min, 773 K) as a function of NO pressure fed to 5.9 cm$^3$ (solid symbols) and 12 cm$^3$ (hollow symbols) quartz reactors.

Two different quartz reactors of similar shapes with different bulb sizes leading to reactor volumes of 5.9 and 12 cm$^3$ were used (FIGS. 1A-1B). FIG. 7A shows the effect of reactor volume on $C_2H_6$ conversion and $C_2H_4$ selectivity. The $C_2H_6$ conversion increased somewhat non-linearly with reactor volume, without significant effects on $C_2H_4$ selectivity at a given conversion when NO is included. The conversion at 0.005 kPa NO was about 4 to 40 times higher than the conversion at 0 kPa NO, depending on the reactor volume. $C_2H_4$ is the major product, and the selectivity to $C_2H_4$ was 95% at 2% conversion but it decreased to 80% at 50% conversion. These results show that reactor volume can increase $C_2H_6$ conversion without affecting the high $C_2H_4$ selectivity. Similar effects of the reactor volume on $C_3H_8$ conversion and alkene selectivity ($C_3H_8+C_2H_4$) are shown in FIG. 7B.

Figure 8A:
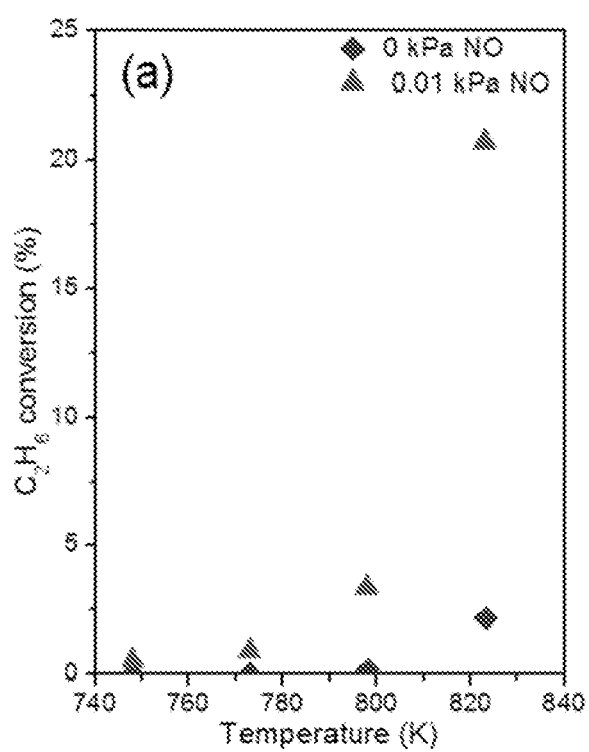
FIG. 8A shows $C_2H_6$ conversion as a function of temperature at 0 (lozenges) or 0.01 kPa (triangles) NO fed to a 12 cm$^3$ quartz reactor (3 kPa $C_2H_6$, 10 kPa $O_2$, 30 cc/min).
Figure 8B:
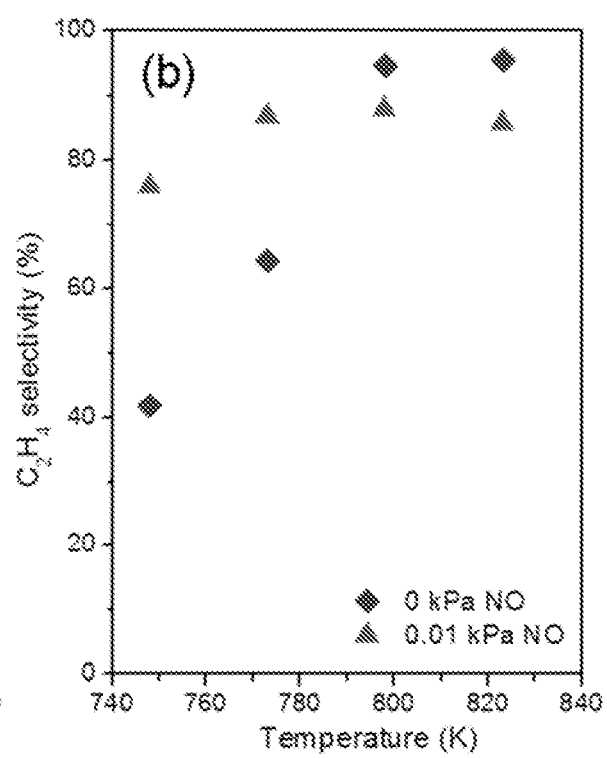
FIG. 8B shows $C_2H_4$ selectivity during conversion of $C_2H_6$ as a function of temperature at 0 (lozenges) or 0.01 kPa (triangles) NO fed to a 12 cm$^3$ quartz reactor (3 kPa $C_2H_6$, 10 kPa $O_2$, 30 cc/min).

Example 5: Effect of Reactor Temperature $C_2H_6$ ODH reactions were performed by flowing 3 kPa $C_2H_6$, 10 kPa $O_2$ and 0 or 0.01 kPa NO, with He as diluent and a 30 cc/min total inlet flow rate at moderate temperatures (723-823 K). FIGS. 8A-8B show the effect of temperature on $C_2H_6$ conversion and selectivity to products. The $C_2H_6$ conversion increases sharply with reaction temperatures for both absence and presence of NO, because of a greater thermodynamic driving force to overcome the C—H activation energies, but the conversions are much higher with NO than without NO. The peak $C_2H_4$ selectivity (95%) occurred at intermediate temperature (773 K with 0.01 kPa NO), because $C_2H_4$ converts to $CO_x$ at higher conversions with further increase in reaction temperatures. These results show that reaction temperatures influence both $C_2H_6$ conversion and $C_2H_4$ selectivity. Similar effects leading to improvement in conversion and selectivity were observed for $C_3H_8$ reactions.

Example 6: Effect of $C_2H_6$ Pressure on $C_2H_6$ Conversion and Product Selectivity $C_2H_6$ ODH reactions were performed by flowing 10 kPa $O_2$, 0 or 0.01 kPa NO and varying the $C_2H_6$ pressure from 1.5 to 11 kPa with He as diluent and a total inlet flow rate of 30 cc/min at 823 K. FIGS. 9A-9B show the effect of $C_2H_6$ pressure on $C_2H_6$ conversion and product selectivity. $C_2H_6$ conversions decrease with $C_2H_6$ pressure at low pressure and then increase weakly. The $C_2H_4$ selectivity remains nearly independent of $C_2H_6$ pressure at 0.01 kPa NO, while it increases with $C_2H_6$ pressure in the low $C_2H_6$ pressure range with 0 kPa NO (FIG. 7B). Similar non-monotonic effect of alkane pressure on conversion at a given total flow rate was observed for $C_3H_8$; the conversion first decreased and then increased.

Example 7: Effect of $O_2$ Pressure on $C_2H_6$ Conversion and Product Selectivity $C_2H_6$ ODH reactions were performed by flowing 3 kPa $C_2H_6$, 0 or 0.01 kPa NO and 1-18 kPa $O_2$ pressure with He as diluent and a total inlet flow rate of 30 cc/min at 823 K. FIGS. 10A-10B show the effect of $O_2$ pressure on $C_2H_6$ conversion and product selectivity. Slight increases in both $C_2H_6$ conversion and $C_2H_4$ selectivity are observed with increasing $O_2$ pressure with a concomitant decrease in aldehydes and carbon oxides.

Example 8: Effect of Water Vapor Pressure on $C_2H_6$ Conversion and Product Selectivity $C_2H_6$ ODH reactions were performed by flowing 3 kPa $C_2H_6$, 10 kPa $O_2$, 0.01 kPa NO and 0 to 10 kPa pressure of $H_2O$ vapor with He as diluent and a total inlet flow rate of 30 cc/min at 873 K. FIGS. 11A-11B show the effect of water vapor pressure on $C_2H_6$ conversion and product selectivity. The $C_2H_6$ conversion increases significantly with increasing water vapor pressure, along with a slight improvement in $C_2H_4$ selectivity, despite higher conversion. These results show that water vapors promote radicals involved in the homogeneous ODH reactions, leading to improved reaction rates and selectivity.

Example 9: Effect of Cofeeding NO in the Presence of Catalytic or Inert Solids

Figure 12:
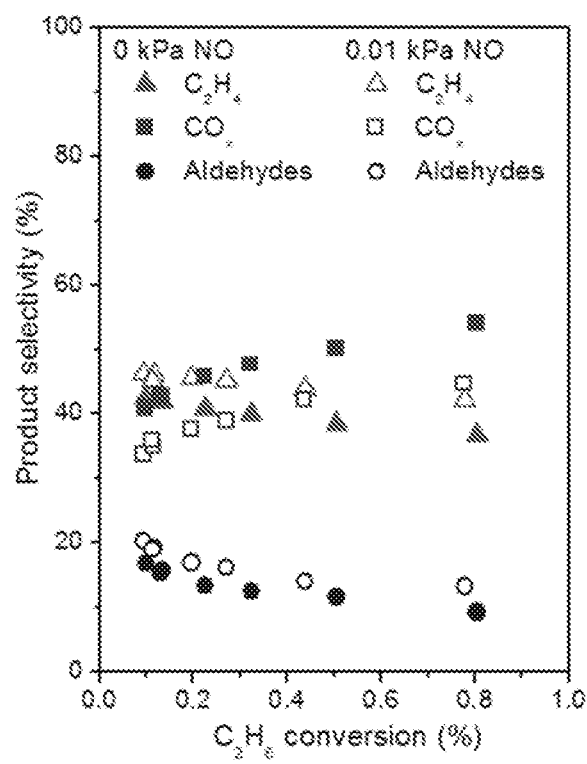
FIG. 12 shows selectivity of $C_2H_6$ oxidation products as a function of $C_2H_6$ conversion on $MoO_3/SiO_2$ at 0 (closed symbols) and 0.01 (open symbols) kPa NO fed to a 5.9 cm$^3$ reactor (748 K, 3 kPa $C_2H_6$, 3 kPa $O_2$, 30 cc/min).

FIGS. 12A-12B show the product selectivity as a function of conversion for $C_2H_6$ ODH on $MoO_x/SiO_2$ catalysts without NO and with 0.01 kPa NO, while keeping other experimental details constant. The $C_2H_4$ selectivity at a given conversion improved slightly with NO pressure, suggesting that gas-phase radical initiator effects on NO can also be observed in the presence of a parallel heterogeneous catalytic reaction.

The effect of inert solids was assessed by filling quartz reactor with nitric acid washed $SiO_2$ powder that was found to be inert, relative to $VO_x/SiO_2$ and $MoO_x/SiO_2$ catalysts for $C_2H_6$ ODH reaction.

Figure 13A:
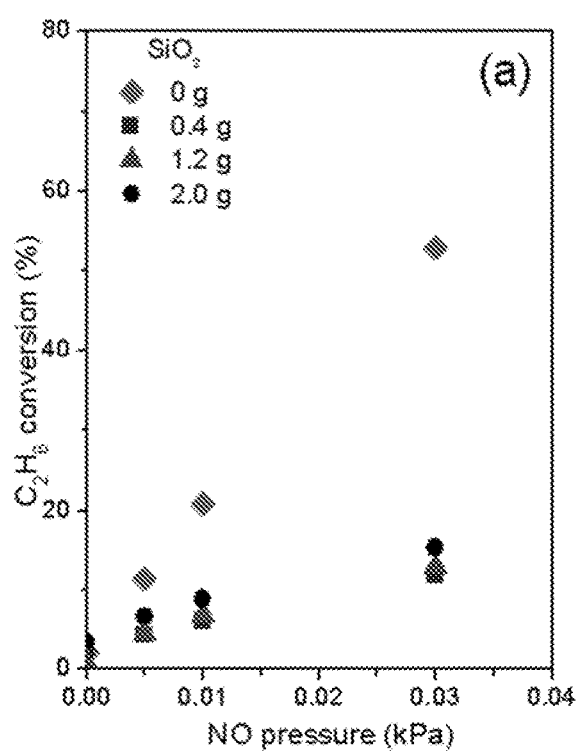
FIG. 13A. shows $C_2H_6$ conversion as a function of NO pressure at different weights of $SiO_2$ held within a 12 cm$^3$ reactor (3 kPa $C_2H_6$, 10 kPa $O_2$, 0-0.03 kPa NO, 30 cc/min, 823 K). Symbol representation: Lozenge, 0 g ($SiO_2$ weights); square, 0.4 g ($SiO_2$ weights); triangle, 1.2 g ($SiO_2$ weights); and circle, 2.0 g ($SiO_2$ weights).
Figure 13B:
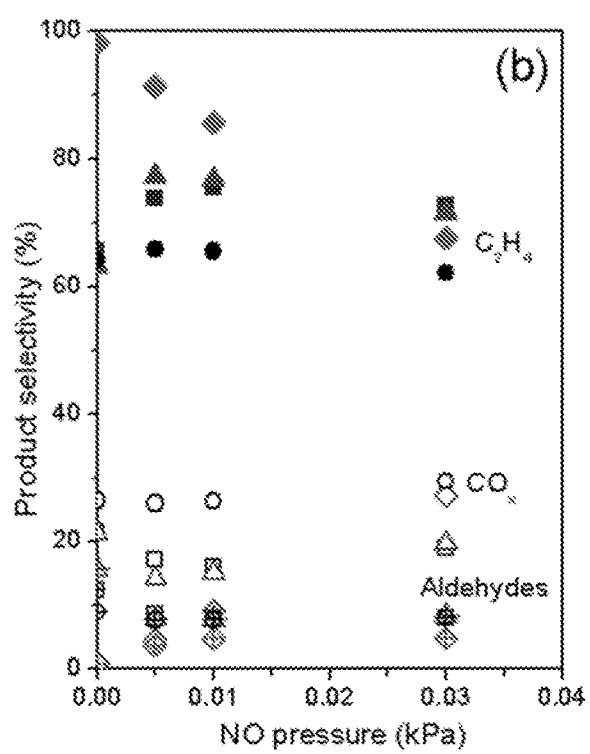
FIG. 13B shows product selectivity as a function of NO pressure at different weights of $SiO_2$ held within a 12 $cm^3$ reactor (3 kPa $C_2H_6$, 10 kPa $O_2$, 0-0.03 kPa NO, 30 cc/min, 823 K). Symbol representation: Solid, $C_2H_4$; open, $CO+CO_2$; and crossed, $CH_3CHO+HCHO$.

FIGS. 13A-13B show $C_2H_6$ conversion and product selectivity as a function of NO pressure at different weights of $SiO_2$ added to the reactor at 823 K. Adding the $SiO_2$ decreases $C_2H_6$ conversion, suggesting that empty volume without surfaces facilitates the gas-phase radical based ODH pathways more efficiently (FIG. 11A). The effect of inert addition was not linear with the decrease in empty volume, suggesting non-linear effects of empty volume on reaction rates, and some contributions from the weak reactivity of the $SiO_2$ material used. The $C_2H_4$ selectivity for empty and filled reactors (with different weights of $SiO_2$) shows weak dependences on NO pressure, except at high conversions beyond 20%.

Example 10: Oxygenates Selectivity and Production of Propylene Oxide

Figure 14:
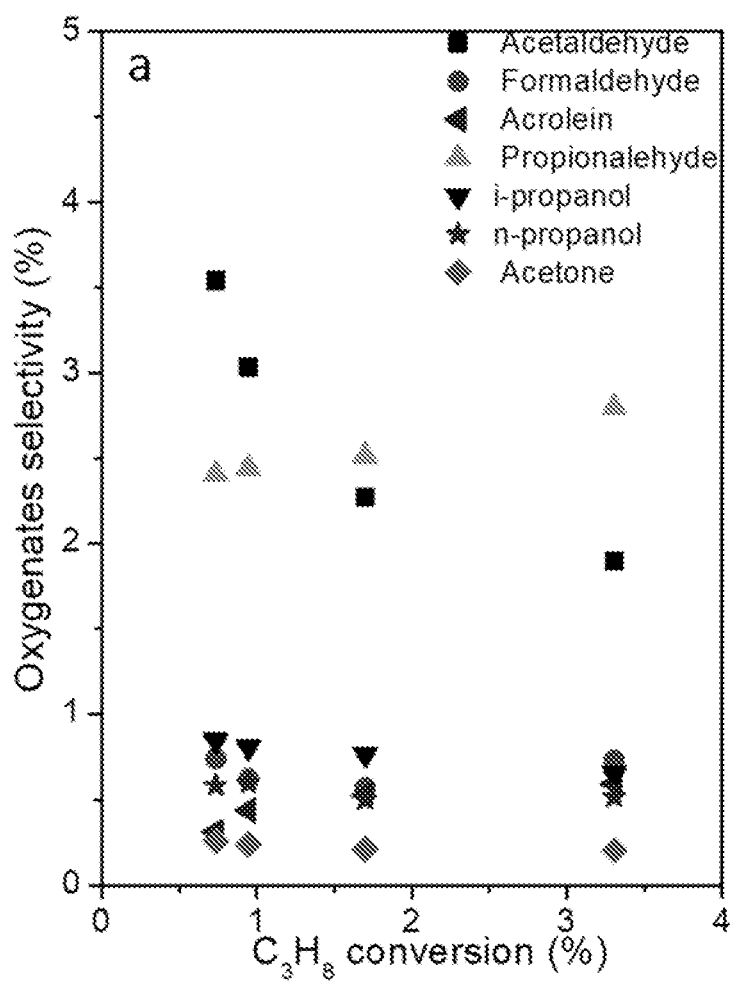
FIG. 14 shows the selectivity in formation of oxygenates in the activation of $C_3H_8$ as a function of conversion in an empty 12 $cm^3$ reactor with 0.005 kPa NO at 773 K, 3 kPa $C_3H_8$, and 10 kPa $O_2$.
Figure 15:
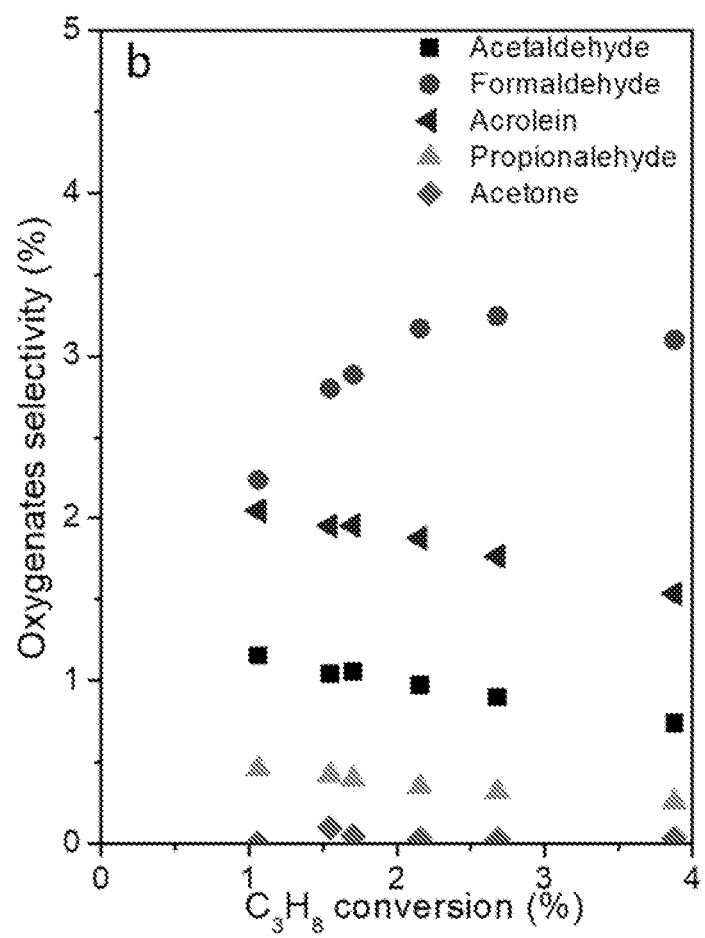
FIG. 15 shows the selectivity in formation of oxygenates in the activation of $C_3H_8$ as a function of conversion in an empty 12 $cm^3$ reactor on $V_2O_5$ catalyst without NO feed at 773 K, 3 kPa $C_3H_8$, and 10 kPa $O_2$.
Figure 16:
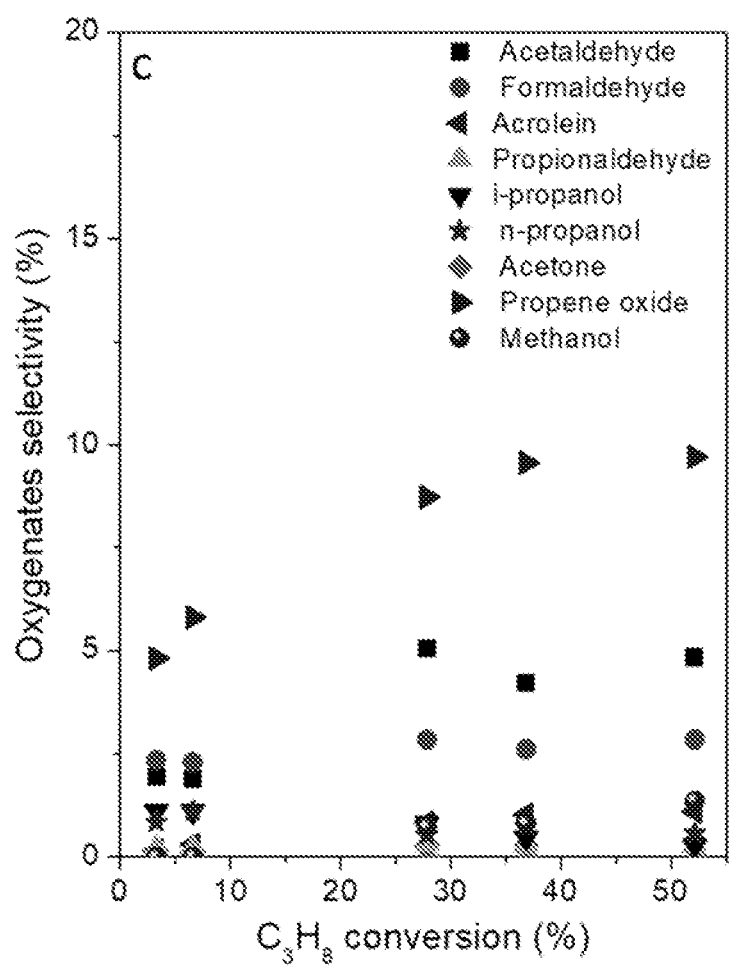
FIG. 16 shows oxygenates formation selectivity as a function of conversion of propane at 723 K in an empty 120 $cm^3$ quartz reactor with 0.005 kPa NO, 3 kPa $C_3H_8$, 10 kPa $O_2$.

The selectivity in the formation of oxygenates in the activation of $C_3H_8$ in an empty 12 cm$^3$ reactor with 0.005 kPa NO, and on $V_2O_5$ catalyst without NO feed, at 773 K, 3 kPa $C_3H_8$, and 10 kPa $O_2$ are shown in FIGS. 14 and 15. FIG. 16 shows oxygenates selectivity as a function of conversion at 723 K in an empty 120 cm$^3$ quartz reactor with 0.005 kPa NO, 3 kPa $C_3H_8$, 10 kPa $O_2$

Example 11: Conversion of $C_2H_4$ and $CH_3OH$ to $C_3H_6$ in a Gas-Phase OCP Reaction Homogeneous gas-phase OCP reactions of $C_2H_4$ (40 kPa) and $CH_3OH$ (5 kPa) were performed in the presence of 5 kPa $O_2$ and 300 ppm NO at 60 cm$^3$ min$^{-1}$ total flow rate in a 12 cm$^3$ empty U-tube quartz reactor at two different temperatures (723 K and 773 K). Feed gases (i.e., $C_2H_4$, $O_2$, NO, and diluent helium) were flown using an electronic mass flow controller. Liquid methanol was evaporated in the flowing stream of feed gases to carry out the gas-phase OCP reactions. Products including $C_3H_6$ and $C_3H_8$, as shown in Table 1 below, were obtained. It revealed that NO mediated radical reactions can also be used for C—C bond formation to prepare valuable longer-chain alkenes.

TABLE 1

Measured reactant conversion and coupling product selectivity in NO mediated homogeneous coupling of $C_2H_4$ and $CH_3OH$.

| Temperature (K) | $CH_3OH$ conversion (%) | $C_2H_4$ conversion (%) | $C_3H_6$ selectivity (%) | $C_3H_8$ selectivity (%) |
|---|---|---|---|---|
| 723 | 0.67 | 0.15 | 6.5 | 10.5 |
| 773 | 4.5 | 1.0 | 7.7 | 1.8 |

Example 12. $C_3H_8$ Activation Rates and Selectivities in $C_3H_8$—$O_2$—NO Reactions FIGS. 17A and 17B shows the effect of NO pressure on $C_3H_8$ conversion and product selectivity in empty flow reactors of two different sizes (6 and 12 cm$^3$ volumes). At the given reaction conditions (773 K, 3 kPa $C_3H_8$, 10 kPa $O_2$, 30 cm$^3$ min$^{-1}$), $C_3H_8$ exhibits conversions below 0.1% in the absence of NO, but the introduction of 0.005 kPa NO increases the conversion by factors of 35 and 20 for the 6 and 12 cm$^3$ reactors, respectively. The incorporation of NO leads to additional $C_3H_8$ reactions that are up to two or more orders of magnitude higher than the number of NO molecules added, depending on residence times and alkane pressures used, which suggests that NO acts as a catalyst instead of getting stoichiometrically consumed in the reaction. This catalytic role of $NO_x$ in hydrocarbon conversion has been proposed and probed mechanistically in many previous studies. The $C_3H_8$ conversion increases with increasing NO pressure and is greater for the larger reactor, suggesting that reactions proceed in the gas-phase via homogeneous pathways enabled by NO or its oxidation products. The conversions increase more significantly than reactor volumes (FIG. 17A) because rates are higher at longer residence times; such non-linear residence time effects are further probed in Section 4. $C_3H_8$—$O_2$ reactions at 0.005 kPa NO and conversions below 5% exhibit $C_3H_6$ and $C_2H_4$ selectivity near 80% and 10%, respectively (FIG. 17B), total $C_1$-$C_3$ oxygenates selectivities near 7%, and total CO and $CO_2$ selectivity below 3%. The $C_3H_6$ selectivity decreases weakly with conversion, consistent with higher yields than those typically attained on oxide catalysts, as also reported in the case of boron nitride catalysts. The formation of $C_2H_4$ is consistent with C—C bond cleavage typically observed when homogeneous pathways mediate $C_3H_8$ activation, which point to mechanistic similarities between NO catalyzed reactions and the homogeneous reactions previously reported. Higher NO feed concentrations enhance $C_3H_8$ conversion rates more significantly but cause slight decrease in $C_3H_6$ selectivity at low conversions (FIG. 17B), suggesting that an optimum low NO concentration maximizes the alkene selectivity at a given conversion.

Large enhancements in rates of alkane activation by $NO_x$ have studied previously for the direct conversion of $CH_4$ to oxygenate such as HCHO. The $NO_x$ catalyzed reactions led to greater HCHO selectivity than heterogeneous routes, but the yields remained well below 10% and significant side reactions that introduced nitrogen into hydrocarbons were observed due to large $NO_x$ feed concentrations up to 5 kPa. We show here that much smaller NO concentrations can be used to selectively convert $C_3H_8$ to alkenes (FIG. 17B). Such small concentrations of NO are present as impurities in industrial exhaust gases that may be added to hydrocarbons and $O_2$ to carry out the desired oxidative conversions. For example, power plant boilers and other sources such as industrial boilers, incinerators and gas turbines operating at high temperatures produce $NO_x$ by oxidizing $N_2$ or nitrogen containing fuels, leading to concentrations up to 300 and 1000 ppm at operating temperatures of 1350 K and 1750 K, respectively. Flue gases from these sources can be mixed with $C_3H_8$—$O_2$ mixtures for production of alkenes and other oxygenates using $NO_x$ at much lower temperatures, and for potentially avoiding more expensive $NO_x$ treatments.

Figure 18A:
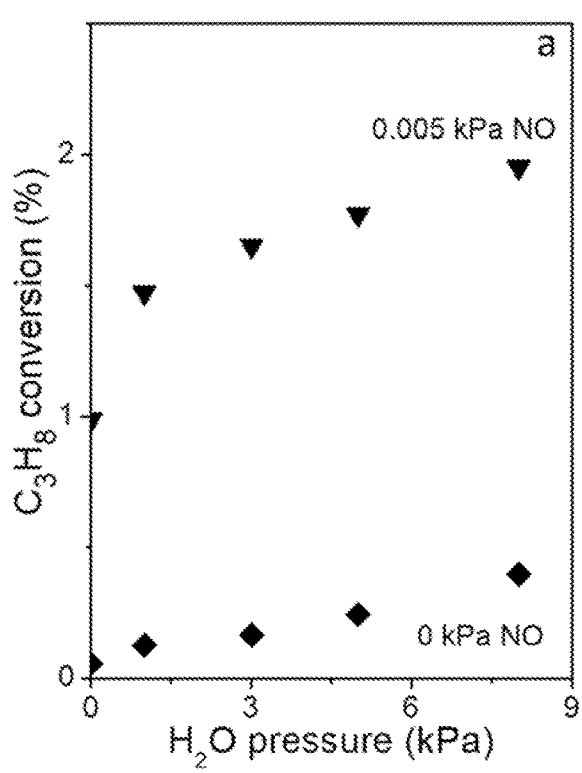
FIG. 18A shows $C_3H_8$ conversion as a function of co-fed $H_2O$ pressure (at 30 $cm^3$ $min^{-1}$), (diamonds—0 kPa NO, triangles—0.005 kPa NO; 773 K, 3 kPa $C_3H_8$, 10 kPa $O_2$, 0-8 kPa $H_2O$, 6 $cm^3$ reactor).
Figure 18B:
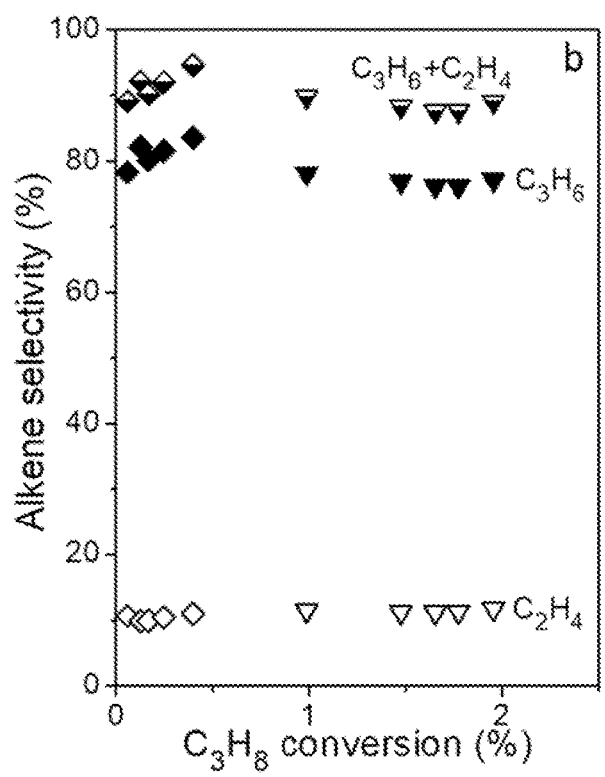
FIG. 18B shows alkene selectivity as a function of $C_3H_8$ conversion at different residence times (diamonds—0 kPa NO, triangles—0.005 kPa NO; 773 K, 3 kPa $C_3H_8$, 10 kPa $O_2$, 0-8 kPa $H_2O$, 6 $cm^3$ reactor).

The mechanism of $NO_x$ catalyzed conversions hydrocarbons such as $CH_4$ involve the generation of OH radicals. These radicals have been detected by laser induced fluorescence measurements for $CH_4/O_2/NO_x$ reactions and their role as predominant abstractors of H atoms from strong C—H bonds has been determined from kinetic simulations. The OH radicals generated from $H_2O$ and $O_2$ in alkali promoted oxides and molten salt catalysts at high temperatures have also been shown to activate hydrocarbons. Therefore, we probe the role of $H_2O$ in further enhancing $NO_x$ mediated $C_3H_8$ conversions by co-feeding $H_2O$ to $C_3H_8$—$O_2$ reactants with and without $NO_x$ catalysts, as shown in FIGS. 18A-18B. When no $H_2O$ is co-fed (0 kPa $H_2O$ in FIG. 18A), the $C_3H_8$ conversion is near 1% for 0.005 kPa $NO_x$, which is much higher than conversion without $NO_x$. At this conversion, the average pressure of $H_2O$ produced from $C_3H_8$—$O_2$ reactions are near 0.01 kPa $H_2O$, which is much less than the co-fed water pressures. The addition of 1 kPa $H_2O$ for 0.005 kPa $NO_x$ increases the conversions to nearly 1.5%; for reactions without $NO_x$, the conversion increase is much smaller. Further increase in co-fed $H_2O$ pressure increases the $C_3H_8$ conversion with slightly greater sensitivity for reactions with $NO_x$. Thus, $H_2O$ enhances reaction rates more significantly when $NO_x$ is present, suggesting that it acts as a promoter or a co-catalyst for $NO_x$ catalyzed OH radical generation. The alkene selectivities remain similar for reactions with and without $NO_x$ and exhibit weak sensitivity to conversion (FIG. 18B), suggesting that similar reactive species can be responsible for alkane activations in both cases. These reactive species have been proposed and shown to be OH radicals in previous homogeneous reaction studies.

Figure 19A:
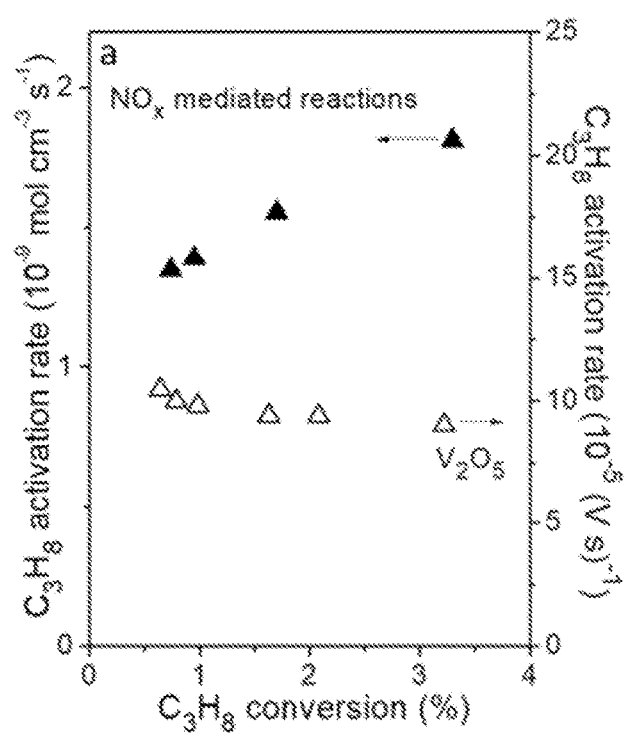
FIG. 19A shows $C_3H_8$ activation rates as a function of $C_3H_8$ conversion, in 12 $cm^3$ empty reactor with 0.005 kPa NO (closed symbols) and on $V_2O_5$ catalyst without NO (open symbols) (773 K, 3 kPa $C_3H_8$, 10 kPa $O_2$, 30-150 $cm^3$ $min^{-1}$). Dashed curves represent best-fits to the form of Equation 2.
Figure 19B:
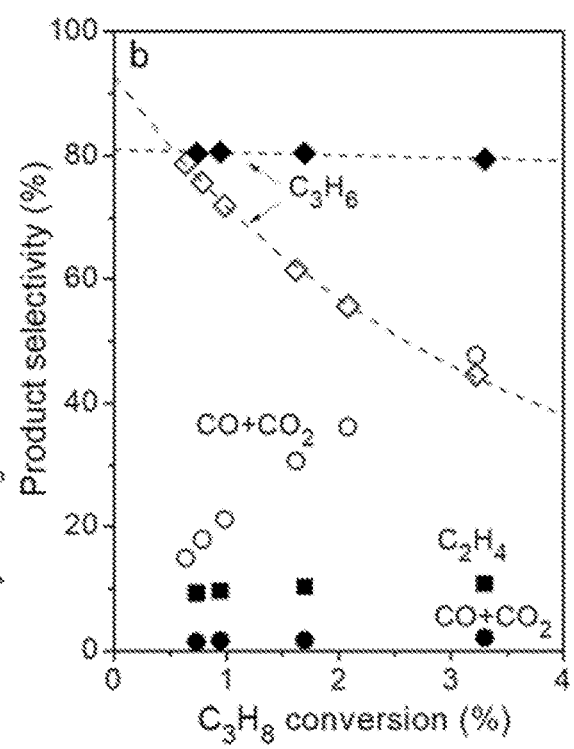
FIG. 19B shows selectivity to alkenes, CO and $CO_2$ as a function of $C_3H_8$ conversion, in 12 $cm^3$ empty reactor with 0.005 kPa NO (closed symbols) and on $V_2O_5$ catalyst without NO (open symbols) (773 K, 3 kPa $C_3H_8$, 10 kPa $O_2$, 30-150 $cm^3$ $min^{-1}$). Dashed curves represent best-fits to the form of Equation 2.

Example 13. Differences in Rates and Selectivity Between $NO_x$ Mediated Pathways and $V_2O_5$ Catalysts $C_3H_8$ activation on vanadium-based oxide catalysts occurs via Mars van Krevelen redox cycles, where lattice oxygen species shown in Table 2 (V=O* species) act as predominant H-abstractors. C—H activations at these sites lead to reduced centers existing as OH pairs or as O-vacancies formed by dihydroxylations at OH pairs. These reduced centers are re-oxidized by rapid $O_2$ activations to restore the V=O* sites. The rapid nature of the re-oxidation steps leads to most of the catalyst existing as V=O* and nearly fixed number of these abstractors at different reaction conditions. In contrast, the $NO_x$ mediated cycles lead to OH radicals as predominant abstractors of strong C—H bonds in $C_3H_8$. The concentration of these abstractors varies with reaction conditions due to changes in concentrations of sacrificial H atom donors to $NO_2$ and presence of $H_2O$. These differences influence how change in $C_3H_8$ conversion via changing residence time affects reaction rates in the two types of reactions. FIGS. 19A-19B shows $C_3H_8$ activation rates and product selectivity as a function of $C_3H_8$ conversion for different flow rates (30-150 $cm^3$ $min^{-1}$) in an empty reactor with 0.005 kPa NO and on $V_2O_5$ catalyst without NO at identical temperature and reactant pressures (773 K, 3 kPa $C_3H_8$, 10 kPa $O_2$). Rates on $V_2O_5$ decreased slightly with increased conversion (FIG. 19A), consistent with the inhibition of C—H activation by products such as $H_2O$ via their adsorption on active lattice oxygens. In contrast, the $C_3H_8$ activation rates in $NO_x$ promoted homogeneous reactions increased with conversion, suggesting a corresponding increase in the concentration of OH radical species that abstract H-atoms from alkanes.

Figure 25A:
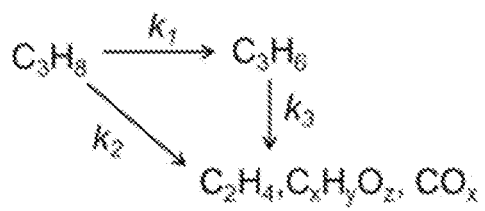
FIG. 25A depicts products formed in oxidative conversion of $C_3H_8$, via all $\cdot C_3H_7$ radicals.
Figure 25B:
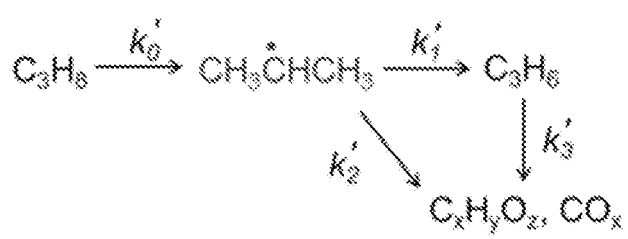
FIG. 25B depicts products formed in oxidative conversion of $C_3H_8$, via secondary $\cdot C_3H_7$ radicals.
Figure 25C:
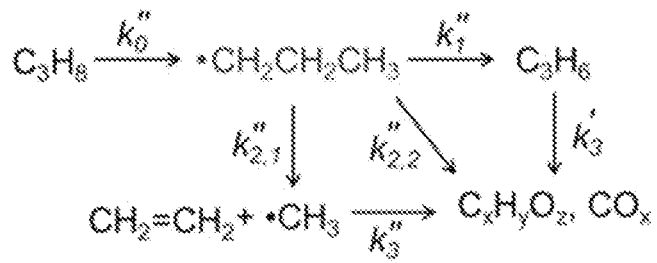
FIG. 25C depicts products formed in oxidative conversion of $C_3H_8$, via primary $\cdot C_3H_7$ radicals.

The homogeneous and heterogeneous systems also exhibit large differences in selectivity trends (FIG. 19B), which can be interpreted using the likely sequence of product formation shown in FIGS. 25A-25C. The selectivity to $C_3H_6$ product at zero conversion represents the fraction of primary $C_3H_8$ activations that branch to this product. The decrease in $C_3H_6$ selectivity with increasing conversion represents sequential conversion of $C_3H_6$ to secondary products (FIG. 25A). A balance over the moles of products, when their formation rates can be represented by lumped first-order rate constants for parallel conversions of $C_3H_8$ ($k_1$, $k_2$, FIG. 25A) and sequential conversion of $C_3H_6$ ($k_3$), lead to selectivity at zero conversion ($S_{C_3H_6}^0$) given by:

$$S_{C_3H_6}^0 = \frac{k_1}{k_1 + k_2} = \frac{1}{1 + \frac{k_2}{k_1}} \quad (1)$$

and the selectivity ($S_{C_3H_6}$) at finite conversions ($X_{C_3H_8}$) given by:

$$S_{C_3H_6} = \frac{S_{C_3H_6}^0}{\left(1 - S_{C_3H_6}^0 \frac{k_3}{k_1}\right) X_{C_3H_8}} \left((1 - X_{C_3H_8})^{S_{C_3H_6}^0 \frac{k_3}{k_1}} - (1 - X_{C_3H_8})\right) \quad (2)$$

Regression of $S_{C_3H_6}$ data in FIG. 19B to the form of Equations 1 and 2 provides rate-constant-ratios that represent numerical descriptors of the selectivity trends, where smaller $k_2/k_1$ and $k_3/k_1$ values represent higher selectivity at zero conversion and weaker selectivity decrease with increasing conversion, respectively.

Example 14. Effects of Reactant Pressures on Rates and Selectivity

The effect of $O_2$ pressure on $C_3H_8$ activation rates in the 12 $cm^3$ quartz reactor at different temperatures is shown in FIG. 20A (773, 788 and 798 K; 60 $cm^3$ $min^{-1}$, 0.005 kPa NO, 3 kPa $C_3H_8$, 1-15 kPa $O_2$). At each of these temperatures, rates increase with $O_2$ pressure at pressures less than 5 kPa $O_2$ but become nearly insensitive to $O_2$ pressure at higher pressures. FIG. 20B shows product selectivities as a function of conversion for different $O_2$ pressures at 798 K. Higher $O_2$ pressures lead to higher $C_3H_6$ selectivity and correspondingly lower $C_2H_4$ selectivity, such that the sum of $C_3H_6$ and $C_2H_4$ selectivity remains nearly independent of $O_2$ pressure (FIG. 20B; 798 K). The slopes of trend-lines for the effect of conversion on selectivity are not affected less significantly by $O_2$ pressures than the intercepts. These results suggest that higher $O_2$ pressures increase the $C_3H_8$ activation rates slightly (FIG. 20A) and exhibit only small effects on the rates of activation of $C_3H_6$ relative to $C_3H_8$ greatly ($k_3/k_1$ values indicated by slopes of dashed curves in FIG. 20B). Instead, the most significant effect of $O_2$ involves altering the branching between C—H activation and C—C bond cleavage in primary $.CH_2CH_2CH_3$ radicals (steps represented by constants $k_1$" and $k_{2,1}$" FIG. 25C). These primary radicals are unstable and undergo a second C—H activation to form $C_3H_6$ even by weak abstractors such as $O_2$. Higher $O_2$ pressures increases the rate of this bimolecular C—H activation over monomolecular C—C cleavage.

The effect of $C_3H_8$ pressure on $C_3H_8$ activation rates in 12 $cm^3$ quartz reactor at different temperatures is shown in FIG. 21A (773, 788 and 798 K; 60 $cm^3$ $min^{-1}$, 0.005 kPa NO, 0.6-11 kPa $C_3H_8$, 10 kPa $O_2$). $C_3H_8$ activation rates exhibit a supra-linear increase with $C_3H_8$ pressure, suggesting that higher alkane concentrations increase concentrations of OH radicals that activate alkanes because more sacrificial species for activating $NO_2$ (step 2, Schemes 1 and 4) and more $H_2O$ is present at a given conversion when the alkane pressure is higher. FIG. 21B shows $C_3H_6$ and $C_2H_4$ selectivities remain nearly independent of $C_3H_8$ pressure above 3 kPa at 798 K.

Figure 22A:
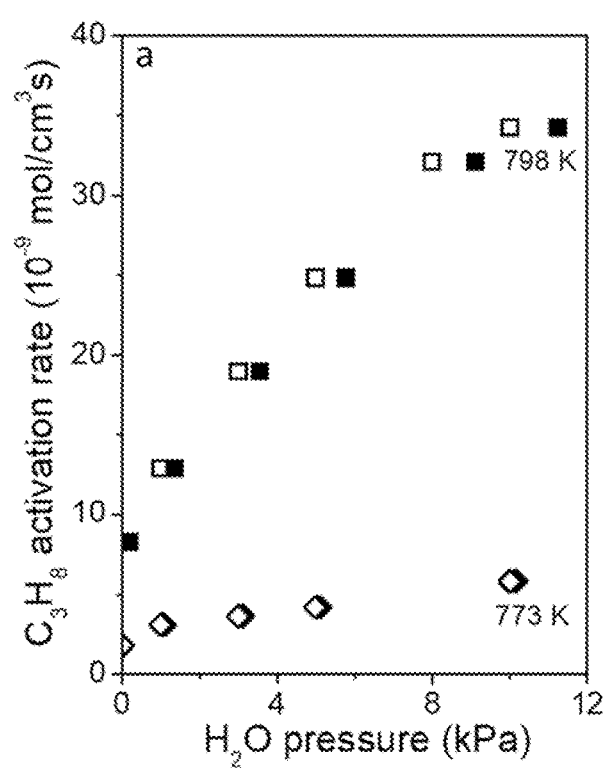
FIG. 22A shows $C_3H_8$ activation rates as a function of added $H_2O$ pressure (open symbols), and sum of added and formed $H_2O$ pressure (closed symbols) at 30 $cm^3$ $min^{-1}$ flow rate, 773, and 798 K. Dashed curves represent best-fits to the form of Equation 2.
Figure 22B:
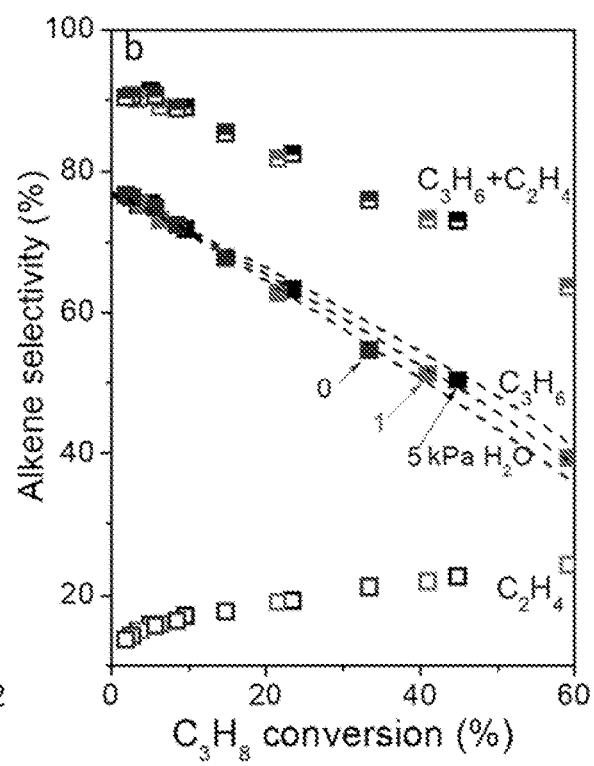
FIG. 22B shows alkene selectivity as a function of conversion for 20-100 $cm^3$ $min^{-1}$ at 798 K, 0-5 kPa added $H_2O$, (0.005 kPa NO, 3 kPa $C_3H_8$, 10 kPa $O_2$, 12 $cm^3$ reactor). Dashed curves represent best-fits to the form of Equation 2.

The effect of $H_2O$ pressure from $H_2O$ co-fed with reactants and formed from $C_3H_8$—$O_2$ conversions on rates and selectivity are shown in FIGS. 22A-22B. The reaction rates increase significantly with added $H_2O$ pressure (FIG. 22A), as also shown by increasing conversions in FIGS. 18A-18B. The rate enhancements by added $H_2O$ are much more significant at higher temperature (FIG. 22A; 773 and 798 K, 30 $cm^3$ $min^{-1}$, 0.005 kPa NO, 0-10 kPa $H_2O$, 3 kPa $C_3H_8$, 10 kPa $O_2$). $H_2O$ formed form reaction shifts the trends only slightly, and the non-zero intercepts in these trends suggest rate enhancements form $NO_x$ catalysis, which is further enhanced by $H_2O$. These results are consistent with the role of $H_2O$ in forming HONO from NO and $NO_2$ in proposed mechanisms (FIGS. 26 and 27) and the facile nature of these steps reported form experimental studies in literature. FIG. 21B shows product selectivities as a function of conversion for added $H_2O$ pressures at 798 K. The $C_3H_6$ and $C_2H_4$ selectivities remain nearly independent of added $H_2O$ (FIG. 21B).

These effects of reactant pressures deviate significantly from ODH reactions on oxide catalysts that involve Mars van Krevelen (MvK) cycles with rate limiting C—H activation at lattice O-atoms of oxides and fast $O_2$ activation.

Figure 26:
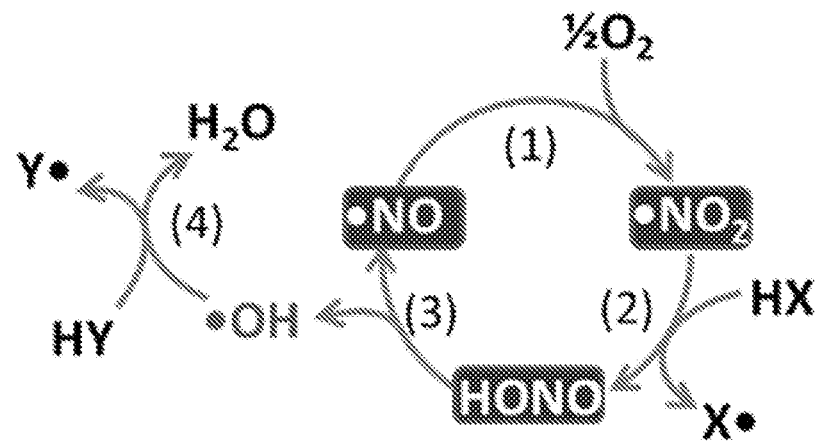
FIG. 26 depicts $NO_x$ catalytic cycles generating OH radicals.
Figure 27:
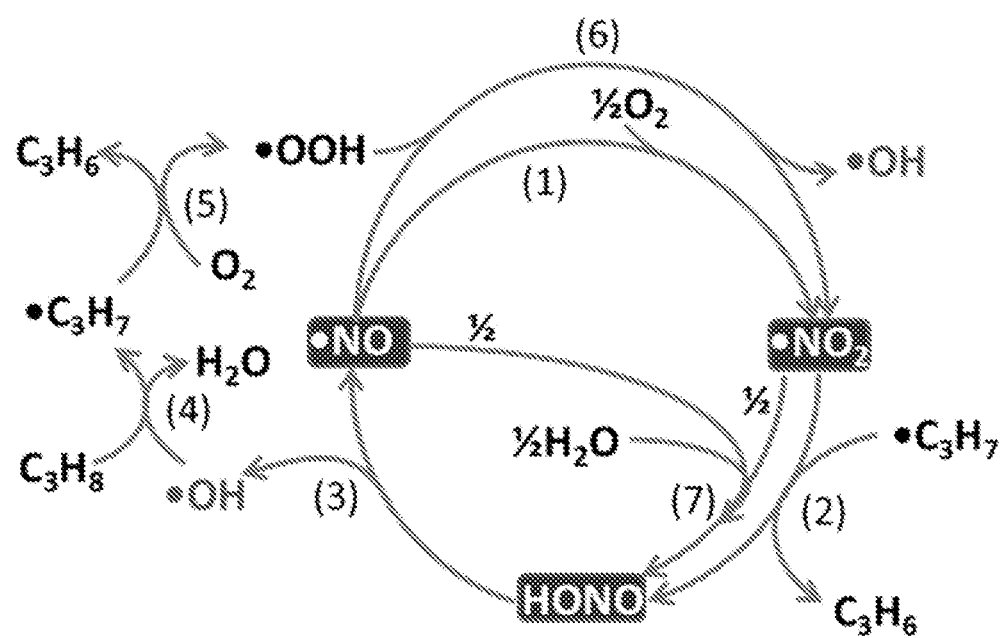
FIG. 27 depicts the primary $C_3H_8$ activation routes in $NO_x$ catalytic cycles.

Such mechanisms invariably exhibit a first-order dependence on alkane pressure and zero-order dependence on $O_2$ pressure. The ODH rates in MvK cycles show small decrease in rates with $H_2O$ pressures due to its adsorption at active sites. The results in $NO_x$ mediated reactions (FIGS. 20A-20B, FIGS. 21A-21B, and FIGS. 22A-22B) and their deviations from heterogeneous reactions on oxides are also observed in trends reported recently for boron nitride and previously for systems in which catalysts generate radicals for homogeneous reactions; they likely originate here from higher concentrations of .OH species in $NO_x$ mediated routes at higher alkane, $O_2$ and $H_2O$ pressures (FIG. 26).

The $C_3H_6$ selectivity data as a function of conversion for the different reactant pressures and reaction temperatures shown in FIGS. 20A-20B, FIGS. 21A-21B, and FIGS. 22A-22B are regressed to the form of Equation 2 to determine rate-constant-ratios, which are shown as a function of reactant pressures and reciprocal temperature in FIGS. 23A-23B and 24A-24B, respectively. These data are used to summarize the effect of reactant pressure on selectivity and derive activation energy differences relevant to selectivity via effects of temperature on the ratios.

Figure 23A:
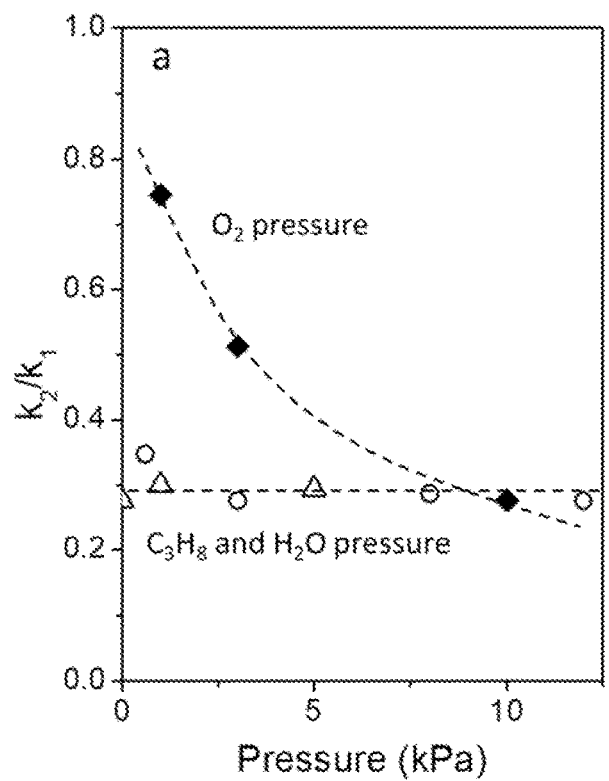
FIG. 23A shows ratios of rate constants $k_2/k_1$ as a function of $C_3H_8$ pressure (circles, 10 kPa $O_2$, 0 kPa $H_2O$), $O_2$ pressure (diamonds, 3 kPa $C_3H_8$, 0 kPa $H_2O$) and $H_2O$ pressure (triangles, 3 kPa $C_3H_8$, 10 kPa $O_2$) at 798 K and 0.005 kPa NO. Dashed curves represent trends.
Figure 23B:
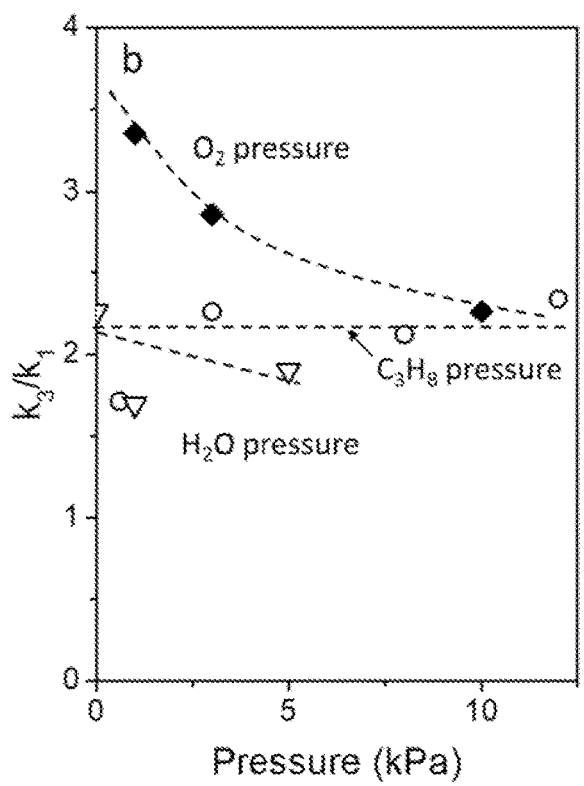
FIG. 23B shows ratios of rate constants $k_3/k_1$, as a function of $C_3H_8$ pressure (circles, 10 kPa $O_2$, 0 kPa $H_2O$), $O_2$ pressure (diamonds, 3 kPa $C_3H_8$, 0 kPa $H_2O$) and $H_2O$ pressure (triangles, 3 kPa $C_3H_8$, 10 kPa $O_2$) at 798 K and 0.005 kPa NO. Dashed curves represent trends.

FIGS. 23A-23B shows the rate constants ratios as function of reactant pressures. $C_3H_8$ and $H_2O$ pressures do not have significant effects on $k_2/k_1$ values (FIG. 23A). Higher $O_2$ pressures lead to much smaller $k_2/k_1$ values, which corresponds to lesser C—C cleavage and greater $C_3H_6$ selectivity (FIG. 20B). These effects suggest that primary .$C_3H_7$ species responsible for $C_2H_4$ formation undergo C—H activation more preferentially than C—C activation when more $O_2$ is present (FIG. 25C). The $k_3/k_1$ values are nearly unaffected by $C_3H_8$ or $H_2O$ pressures (FIG. 23B) but decrease slightly (implying higher selectivity) at higher $O_2$ pressure. These data suggest that using denser feeds with high alkane and $H_2O$ pressures will significantly enhance the rates (FIGS. 21A and 22A) and productivity, while retaining high selectivity and yields. Furthermore, high $O_2$ pressures can be used to decrease $C_2H_4$ selectivity and increase $C_3H_6$ selectivity to values higher than that shown here (FIG. 20B).

Example 15. Effect of Abstractor Strength on Activation Enthalpy Differences for Steps Involving C—H Bonds of Different Strengths FIGS. 24A-24B shows the rate constant ratios $k_2/k_1$ and $k_3/k_1$, representing selectivity for $C_3H_6$ formation over parallel and sequential reactions as a function of reciprocal temperature for identical reactant pressures on $V_2O_5$ catalyst and in $NO_x$ catalyzed reactions. $NO_x$ mediated reactions exhibit larger $k_2/k_1$ values than $V_2O_5$ (FIG. 24A), because generation of primary radicals leads to significant C—C bond cleavage, which results in high $C_2H_4$ selectivity at zero conversion (FIG. 4b). The $k_3/k_1$ values are much larger in $V_2O_5$ than in $NO_x$ mediated reactions, because the latter reactions dampen the secondary reactions of $C_3H_6$ (FIG. 24B).

The effects of temperature on rate constant ratios, at identical reactant pressures in FIGS. 24A-24B ($k_2/k_1$, and $k_3/k_1$ at 0.005 kPa NO, 3 kPa $C_3H_8$, and 10 kPa $O_2$), are expressed as activation enthalpy differences between the parallel or sequential undesired reactions and the $C_3H_6$ formation reaction using the following relations:

$$\frac{k_2}{k_1} = \exp\left(\frac{\Delta S_2^{act} - \Delta S_1^{act}}{R}\right)\exp\left(-\frac{\Delta H_2^{act} - \Delta H_1^{act}}{RT}\right) = \exp\left(\frac{\Delta\Delta S_{21}}{R}\right)\exp\left(-\frac{\Delta\Delta H_{21}}{RT}\right) \quad (3)$$

$$\frac{k_3}{k_1} = \exp\left(\frac{\Delta S_3^{act} - \Delta S_1^{act}}{R}\right)\exp\left(-\frac{\Delta H_3^{act} - \Delta H_1^{act}}{RT}\right) = \exp\left(\frac{\Delta\Delta S_{31}}{R}\right)\exp\left(-\frac{\Delta\Delta H_{31}}{RT}\right) \quad (4)$$

where, $\Delta H_1^{act}$ and $\Delta H_2^{act}$ represent ensemble averaged activation enthalpy for $C_3H_6$ formation and all steps mediating parallel $C_3H_8$ oxidation steps relative to gaseous $C_3H_8$ (FIG. 25C), respectively, $\Delta H_3^{act}$ represents activation enthalpy for $C_3H_6$ oxidation steps relative to gaseous $C_3H_6$, and $\Delta S^{act}$ values represent corresponding activation entropies. The values of activation enthalpy differences relevant to rate constant ratios $k_2/k_1$ ($\Delta\Delta H_{21} = \Delta H_2^{act} - \Delta H_1^{act}$) and $k_3/k_1$ ($\Delta\Delta H_{31} = \Delta H_3^{act} - \Delta H_1^{act}$) derived from slopes of regressed lines in FIGS. 24A-24B are shown in Table 2.

TABLE 2

Activation enthalpy differences between the parallel or sequential reactions and the primary C—H activations derived from regression of rate constants ratios in FIG. 9 to the form of Equation 3 and 4. Uncertainties represent the standard errors.

| Reaction System | $\Delta H_2^{act}$-$\Delta H_1^{act}$ (kJ mol$^{-1}$) | $\Delta H_3^{act}$-$\Delta H_1^{act}$ (kJ mol$^{-1}$) |
| --- | --- | --- |
| $V_2O_5$ | −33 ± 34 | −26 ± 1 |
| $NO_x$ mediated | 15 ± 10 | −3 ± 3 |

REFERENCES CITED

1. Ren, T.; Patel, M.; Blok, K. Olefins from conventional and heavy feedstocks: Energy use in steam cracking and alternative processes, Energy, vol. 31, pp. 425-451 (2006).
2. Jenkins, S. Shale gas ushers in ethylene feed shifts, Chemical Engineering, vol. 119, pp. 17-19 (2012).
3. Cavani, F.; Trifiro, F. The oxidative dehydrogenation of ethane and propane as an alternative way for the production of light olefins, Catalysis Today, vol. 24, pp. 307-313 (1995).
4. Cavani, F.; Ballarini, N.; Cericola, A. Oxidative dehydrogenation of ethane and propane: How far from commercial implementation? Catalysis Today, vol. 127, pp. 113-131 (2007).
5. Ueda, W.; Oshihara, K. Selective oxidation of light alkanes over hydrothermally synthesized Mo-VMO (M=Al, Ga, Bi, Sb, and Te) oxide catalysts, Applied Catalysis A: General, vol. 200, pp. 135-143 (2000).
6. Martinez-Huerta, M.; Gao, X.; Tian, H.; Wachs, I.; Fierro, J.; Banares, M. Oxidative dehydrogenation of ethane to ethylene over alumina-supported vanadium oxide catalysts: Relationship between molecular structures and chemical reactivity, Catalysis Today, vol. 118, pp. 279-287 (2006).
7. Heracleous, E.; Lemonidou, A. Ni—Nb—O mixed oxides as highly active and selective catalysts for ethene production via ethane oxidative dehydrogenation, Part I: Characterization and catalytic performance, Journal of Catalysis, vol. 237, pp. 162-174 (2006).
8. Argyle, M. D.; Chen, K.; Bell, A. T.; Iglesia, E. Ethane oxidative dehydrogenation pathways on vanadium oxide catalysts, The Journal of Physical Chemistry B, vol. 106, pp. 5421-5427 (2002).
9. Argyle, M. D.; Chen, K.; Bell, A. T.; Iglesia, E. Effect of catalyst structure on oxidative dehydrogenation of ethane and propane on alumina-supported vanadia, Journal of Catalysis, vol. 208, pp. 139-149 (2002).
10. Shi, L.; Yan, B.; Shao, D.; Jiang, F.; Wang, D.; Lu, A.-H. Selective oxidative dehydrogenation of ethane to ethylene over a hydroxylated boron nitride catalyst, Chinese Journal of Catalysis, vol. 38, pp. 389-395 (2017).
11. Wachs, I. E. Recent conceptual advances in the catalysis science of mixed metal oxide catalytic materials, Catalysis Today, vol. 100, pp. 79-94 (2005).
12. Baroi, C.; Gaffney, A. M.; Fushimi, R. Process economics and safety considerations for the oxidative dehydrogenation of ethane using the M1 catalyst, Catalysis Today, (2017).
13. Cavani, F.; Trifiro, F. Selective oxidation of light alkanes: interaction between the catalyst and the gas phase on different classes of catalytic materials, Catalysis Today, vol. 51, pp. 561-580 (1999).
14. Liang, Y.; Li, Z.; Nourdine, M.; Shahid, S.; Takanabe, K. Methane Coupling Reaction in an Oxy ☐Steam Stream through an OH Radical Pathway by using Supported Alkali Metal Catalysts, Chem Cat Chem., vol. 6, pp. 1245-1251 (2014).
15. Takanabe, K.; Shahid, S. Dehydrogenation of ethane to ethylene via radical pathways enhanced by alkali metal based catalyst in oxysteam condition, AIChE Journal, vol. 63, pp. 105-110 (2017).
16. Zalc, J. M.; Green, W. H.; Iglesia, E. $NO_x$-Mediated Homogeneous Pathways for the Synthesis of Formaldehyde from $CH_4$—$O_2$ Mixtures, Industrial & engineering chemistry research, vol. 45, pp. 2677-2688 (2006).
17. Otsuka, K.; Takahashi, R.; Yamanaka, I. Oxygenates from light alkanes catalyzed by $NO_x$ in the gas phase, Journal of Catalysis, vol. 185, pp. 182-191 (1999).
18. Sen, A.; Lin, M. $NO_x$-catalyzed partial oxidation of methane and ethane to formaldehyde by dioxygen, Topics in Catalysis, vol. 32, pp. 175-178 (2005).
19. Hjuler, K.; Glarborg, P.; Dam-Johansen, K. Mutually promoted thermal oxidation of nitric oxide and organic compounds, Industrial & Engineering Chemistry Research, vol. 34, pp. 1882-1888 (1995).
20. Cai, H.; Krzywicki, A.; Oballa, M. C. Chemical Engineering and Processing: Process Intensification, vol. 41, pp. 199-214 (2002).
21. Grubert, G.; Kondratenko, E.; Kolf, S.; Baerns, M.; Van Geem, P.; Parton, R. Catalysis Today, vol. 81, pp. 337-345 (2003).
22. Heracleous, E.; Lemonidou, A. Journal of Catalysis, vol. 237, pp. 162-174 (2006).
23. M. López Nieto; P. Botella; M. I. Vazquez; A. Dejoz. Chemical Communication, pp. 1906-1907 (2002).
24. Ishii et al. 1999 A new strategy for alkane oxidation with 02 using N-hydroxyphthalimide (NHPI) as a radical catalyst, Catalysis Surveys from Japan 3: 27-35.
25. Alper, J. The Changing Landscape of Hydrocarbon Feedstocks for Chemical Production: implications for Catalysis: Proceedings of a Workshop, The National Academies Press, pp. 1-130 (ISBN 978-0-309-44479-8|DOI: 10.17226/23555),
26. Emmons, W. D. 1957 The preparation and properties of oxaziranes, Journal of the American Chemical Society, 79(21), pp. 5739-5754.
27. Mosher, M. W.; Bunce, N.J. 1971 The Free Radical Photooximation of Alkanes by Nitrosyl Chloride, Canadian Journal of Chemistry, 49(1), pp. 28-34.
28. Brown, H. C. 1972 Boranes in organic chemistry (Vol. 13), Ithaca, N.Y.: Cornell University Press.
29. J. T. Grant, C. A. Carrero, F. Goeltl, J. Venegas, P. Mueller, S. P. Burt, S. E. Specht, W. P. McDermott, A. Chieregato, I. Hermans; Science, 354 (6319), 1570-1573, 2016.
30. Shi, L.; Wang, D.; Song, W.; Shao, D.; Zhang, W.-P.; Lu, A.-H. Chem Cat Chem 2017, 9, 1788-1793.
31. J. T. Grant, W. P. McDermott, J. M. Venegas, S. P. Burt, J. Micka, S. P. Phivilay, C. A. Carrero, I. Hermans; Chem Cat Chem, 10.1002/cctc.201701140.
32. Deshlahra, P.; Iglesia, E. The Journal of Physical Chemistry, 2016, 120, 16741-16760.
33. A. Leelavathi, Y. Liu, S. Ezenwa, Y. Dang, S. L. Suib, P. Deshlahra; "Influence of Tight Confinement on Selective Oxidative Dehydrogenation of Ethane on MoVTeNb Mixed Oxides", ACS Catal. 2018, 8, 7051-7067.
34. U.S. Pat. No. 5,990,370, US 2017/0106346, U.S. Pat. Nos. 8,105,972, 4,596,787, 4,568,790, 8,519,210, 7,319,179, US 2017/0066700 A1, U.S. Pat. No. 6,518,476 B1, and WO 2017/044711; all of which are incorporated by reference.

INCORPORATION BY REFERENCE

All U.S. and PCT patent application publications and U.S. patents mentioned herein are hereby incorporated by reference in their entirety as if each individual publication or patent was specifically and individually indicated to be incorporated by reference. In case of conflict, the application, including any definitions herein, will control.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing"

are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the embodiments described herein is not intended to be limited to the above Description, but rather is as set forth in the appended claims. Those of ordinary skill in the art will appreciate that various changes and modifications to this description may be made without departing from the spirit or scope of the invention, as defined in the following claims.

We claim:

1. A gas-phase oxidative dehydrogenation (ODH) process for converting an alkane to propylene or propylene oxide, comprising:
    flowing a feed gas through a heated reaction zone within a reactor, wherein the feed gas comprises an alkane, an oxidizing agent, and a radical initiator,
wherein:
    the heated reaction zone has a temperature of 363 to 1000 K;
    the heated reaction zone is a space or a combination of a space and an inert solid surface; and
    the radical initiator is nitric oxide or nitrogen dioxide.

2. The process of claim 1, wherein the alkane is a $C_{1-20}$ alkane.

3. The process of claim 2, wherein the alkane is ethane or propane, and the oxidizing agent is oxygen, nitrous oxide, or carbon dioxide.

4. The process of claim 3, wherein the oxidizing agent is oxygen present at 3 kPa to 50 kPa in the feed gas, and the radical initiator is nitric oxide present at 1 ppm to 500 ppm in the feed gas.

5. The process of claim 1, wherein the feed gas further comprises one or more hydrocarbons, and/or inert diluent, and/or water vapor.

6. The process of claim 5, wherein the inert diluent is helium, nitrogen, carbon dioxide or carbon monoxide.

7. The process of claim 1, wherein the process is performed at 1 to 5 atmospheric pressure.

8. The process of claim 1, wherein the heated reaction zone has a temperature of 363 to 873 K.

9. The process of claim 1, wherein the process is performed in the absence of a solid catalyst.

10. The process of claim 1, wherein the process is performed with the presence of a solid catalyst.

11. The process of claim 10, wherein the solid catalyst is $VO_x/SiO_2$.

12. The process of claim 10, wherein the solid catalyst is used at an amount of 20 wt % to 60 wt %.

13. The process of claim 10, wherein the solid catalyst is used at an amount of 40 wt %.

14. The process of claim 1, wherein the reactor is a straight quartz tube, a U-shaped quartz tube, a straight stainless steel tube, or a U-shaped stainless steel tube.

15. A gas-phase coupling process for converting a hydrocarbon feedstock to an effluent stream, comprising:
    flowing a feed gas comprising a hydrocarbon feedstock, an oxidizing agent, and a radical initiator through a heated reaction zone within a reactor;
wherein:
    the hydrocarbon feedstock comprises an oxygenate, and a $C_1$-$C_6$ alkane or a $C_2$-$C_6$ alkene;
    the effluent stream comprises a $C_7$-$C_{20}$ alkane or a $C_7$-$C_{20}$ alkene or both;
    the heated reaction zone has a temperature of 363 to 1000 K;
    the heated reaction zone is a space or a combination of a space and an inert solid surface, whereby the effluent stream is produced; and
    the radical initiator is nitric oxide or nitrogen dioxide.

16. A gas-phase coupling process for converting an alkene and an oxygenate to a longer carbon-chain alkene or a longer carbon-chain alkane, comprising:
    flowing a feed gas through a heated reaction zone within a reactor, wherein the feed gas comprises an alkene, an oxygenate, an oxidizing agent, and a radical initiator,
wherein:
    the heated reaction zone has a temperature of 363 to 1000 K;
    the heated reaction zone is a space or a combination of a space and an inert solid surface; and
    the radical initiator is nitric oxide or nitrogen dioxide.

17. The process of claim 16, wherein the alkene in the feed gas comprises a $C_{2-20}$ alkene, and the oxygenate in the feed gas comprises $C_{1-6}$ alcohol.

18. The process of claim 16, wherein the lower alkene is propene or ethylene, the oxygenate comprises methanol, ethanol or isopropanol, and the oxidizing agent is oxygen.

19. The process of claim 18, wherein the oxidizing agent is oxygen present at 3 kPa to 50 kPa in the feed gas, and the radical initiator is nitric oxide present at 1 ppm to 500 ppm in the feed gas.

20. The process of claim 16, wherein the feed gas further includes an inert diluent, or water vapor.

21. The process of claim 20, wherein the inert diluent is helium, nitrogen, carbon dioxide, or carbon monoxide.

22. The process of claim 16, wherein the process is performed at 1 to 5 atmospheric pressure.

23. The process of claim 16, wherein the process is performed at a temperature from 363 to 873 K.

24. The process of claim 16, wherein the process is performed in the absence of a solid catalyst.

25. The process of claim 16, wherein the reactor is a straight quartz tube, a U-shaped quartz tube, a straight stainless steel tube, or a U-shaped stainless steel tube.

* * * * *